United States Patent [19]

Ohno et al.

[11] Patent Number: 4,474,802
[45] Date of Patent: Oct. 2, 1984

[54] 5,6,7-TRINOR-4,8-INTER-M-PHENYLENE PROSTAGLANDIN I₂ DERIVATIVES USEFUL IN ANTI-ULCER, HYPOTENSIVE AND PLATELET AGGREGATION INHIBITING COMPOSITIONS

[75] Inventors: Kiyotaka Ohno, Fujisawa; Hiroshi Nagase, Kamakura; Kazuhisa Matsumoto, Fujisawa; Shintaro Nishio, Ebina, all of Japan

[73] Assignee: Toray Industries, Inc., Tokyo, Japan

[21] Appl. No.: 459,226

[22] Filed: Jan. 19, 1983

[30] Foreign Application Priority Data

Jan. 20, 1982 [JP] Japan .................... 57-6150

[51] Int. Cl.³ .................. A61K 31/34; C07D 307/93
[52] U.S. Cl. .................................. 424/285; 549/458
[58] Field of Search .............. 549/458; 424/285; 542/429

[56] References Cited

U.S. PATENT DOCUMENTS 4,301,164  11/1981  Ohno et al. .................... 424/285

FOREIGN PATENT DOCUMENTS 60640  9/1982  European Pat. Off. .

*Primary Examiner*—Henry R. Jiles
*Assistant Examiner*—Bernard Dentz

*Attorney, Agent, or Firm*—Finnegan, Henderson, Farabow, Garrett & Dunner

[57] ABSTRACT

A compound of the formula

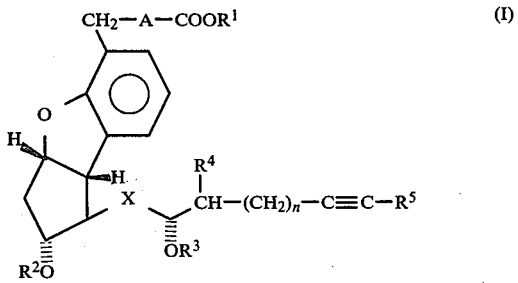

wherein $R^1$ is a pharmaceutically acceptable cation, hydrogen or n-alkyl of 1 to 12 carbon atoms; $R^2$ is hydrogen, acyl of 2 to 10 carbon atoms or aroyl of 7 to 13 carbon atoms; $R^3$ is hydrogen, acyl of 2 to 10 carbon atoms or aroyl of 7 to 13 carbon atoms; $R^4$ is hydrogen, methyl or ethyl; $R^5$ is n-alkyl of 1 to 5 carbon atoms; n is an integer of 0 to 4; A is $-CH_2-CH_2-$ or trans $-CH=CH-$; and X is $-CH_2-CH_2-$ or trans $-CH=CH-$. The compounds are useful in anti-ulcer, hypotensive and platelet aggregation inhibiting compositions.

14 Claims, No Drawings

5,6,7-TRINOR-4,8-INTER-M-PHENYLENE PROSTAGLANDIN $I_2$ DERIVATIVES USEFUL IN ANTI-ULCER, HYPOTENSIVE AND PLATELET AGGREGATION INHIBITING COMPOSITIONS

BACKGROUND OF THE INVENTION

The present invention relates to novel prostaglandin $I_2$ derivatives, more particularly, to 5,6,7-trinor-4,8-inter-m-phenylene prostaglandin $I_2$ derivatives.

Prostaglandin $I_2$, hereinafter referred to as $PGI_2$, of the formula

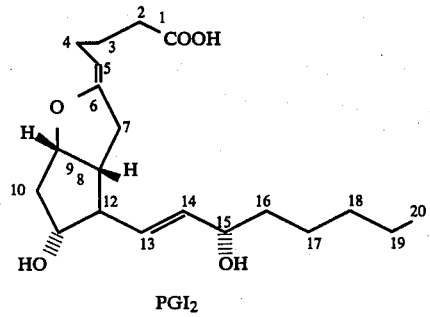

PGI$_2$ was first found by J. R. Vane et. al. in 1976 and is biosynthesized from arachidonic acid via endoperoxide(PGH$_2$ or PGG$_2$) in the vascular wall. PGI$_2$ is well known to show potent activity to inhibit platelet aggregation and to dilate peripheral blood vessels (C & EN, Dec. 20, 1976, page 17 and S. Moncade et al., Nature, 263,633(1976)).

Because of the unstable exo-enolether structure thereof, PGI$_2$ is extremely unstable even in a neutral aqueous solution and is readily converted to 6-oxo-PGF$_{1\alpha}$ which is almost physiologically inactive. Such instability of PGI$_2$ is a big obstacle to its use as a drug. Furthermore, PGI$_2$ is unstable in vivo as well and shows only short duration of action.

The compounds of the present invention are novel PGI$_2$ derivatives in which the exo-enolether moiety characteristic of PGI$_2$ is transformed into "inter-m-phenylene" moiety. In this sense the compounds may be regarded as analogs of PGI$_2$.

The compounds of the present invention feature much improved stability in vitro as well as in vivo in comparison with PGI$_2$. The compounds are highly stable even in an aqueous solution and show long duration of action in vivo. Further, the compounds have advantages over PGI$_2$ for pharmaceutical application because they exhibit more selective physiological actions than PGI$_2$, which has multifarious, inseperable biological activities.

Some prostaglandin $I_2$ derivatives which have 5,6,7-trinor-4,8-inter-m-phenylene structure have already been described in publication by some of the present authors. (Kiyotaka Ohno, Hisao Nishiyama and Shintaro Nishio, U.S. Pat. No. 4,301,164 (1981)). But, the compounds of the present invention, which feature the presence of alkynyl side chain, have more potent physiological activities as well as decreased side effects than the already disclosed compounds analogous to those of the present invention.

It is an object of this invention to provide novel prostaglandin $I_2$ derivatives which are stable and possess platelet aggregation-inhibiting, hypotensive, anti-ulcer and other activities.

Another object of this invention is to provide the compounds improved on physiological efficacy as compared with the compounds which have already been disclosed by some of the present authors.

Other objects and advantages of this invention will be apparent from the description hereinbelow.

SUMMARY OF THE INVENTION

A compound of the formula:

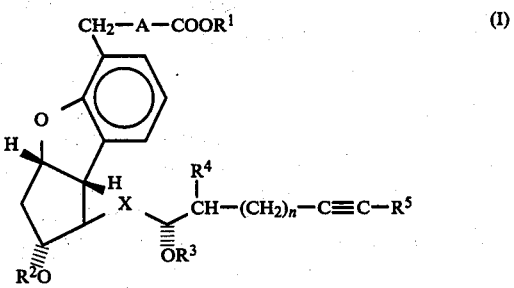

wherein $R^1$ is a pharmaceutically acceptable cation, hydrogen or n-alkyl of 1 to 12 carbon atoms; $R^2$ is hydrogen, acyl of 2 to 10 carbon atoms or aroyl of 7 to 13 carbon atoms; $R^3$ is hydrogen, acyl of 2 to 10 carbon atoms or aroyl of 7 to 13 carbon atoms; $R^4$ is hydrogen, methyl or ethyl; $R^5$ is n-alkyl of 1 to 5 carbon atoms; n is an integer of 0 to 4; A is —CH$_2$—CH$_2$13 or trans —CH=CH—; and X is —CH$_2$—CH$_2$— or trans —CH=CH—.

DETAILED DESCRIPTION OF THE INVENTION

In the compound of the formula (I), examples of the pharmaceutically acceptable cation defined in $R^1$ include a metal cation, an ammonium ion, an amine cation or a quarternary ammonium cation.

Preferred metal cations are alkali metal, for instance, lithium, sodium, potassium and alkaline earth metal, for instance, magnesium and calcium. Other metal ions, for instance, aluminum, zinc and iron are also suitable as cation $R^1$ in the invention.

The pharmacologically acceptable amine cations as $R^1$ are those derived from primary, secondary and tertiary amines. Suitable amines are, by way of example, methylamine, dimethylamine, triethylamine, ethylamine, dibutylamine, tri-isopropylamine, N-methylhexylamine, decylamine, dodecylamine, allylamine, crotylamine, cyclopentylamine, dicyclohexylamine, benzylamine, dibenzylamine, alpha-phenyl-ethylamine, beta-phenyl-ethylamine, ethylene-diamine, diethylenetriamine. Alternatively, preferably included are the analogous aliphatic-, cycloaliphatic- and heterocyclic amines having carbon atoms up to about 18, for instance, 1-methylpiperidine, 4-ethylmorpholine, 1-isopropylpyrrolidine, 2-methylpyrrolidine, 1,4-dimethylpiperazine, 2-methylpiperidine, etc. and the water-soluble amines or the amines having hydrophilic group, for instance, mono-, di- and triethanolamine, ethyldiethylamine, N-butylethanolamine, 2-amino-1-butanol, 2-amino-2-ethyl-1,3-propanediol, tris(hydroxymethyl)aminomethane, N-phenylethanolamine, N-(p-tert-amylphenyl)-diethanolamine, galactamine, N-methylglutamine, N-methylglucosamine, ephedrine, phenylephrine, epinephrine, procaine, etc. and furthermore, basic amino acids, for instance, lysine, arginine, etc.

Examples of the normal alkyl group of 1 to 12 carbon atoms defined in $R^1$ include methyl-, ethyl-, propyl-, butyl-, pentyl-, hexyl-, heptyl-, octyl-, dodecyl group, etc.

Examples of the acyl group of 2 to 10 carbon atoms defined in $R^2$ include acetyl-, propionyl-, butyroyl-, octanoyl- and decanoyl group. The acyl group $R^2$ is, however, not limited to those mentioned above.

Examples of the aroyl group of 7 to 13 carbon atoms defined in $R^2$ include benzoyl-, p-toluoyl-, p-phenylbenzoyl group, etc. The aroyl group $R^2$ is, however, not limited to those mentioned above.

Though $R^3$ has the same meaning as $R^2$, $R^2$ and $R^3$ may be the same substituent or may be different from each other.

Examples of the normal alkyl group of 1 to 5 carbon atoms defined in $R^5$ include methyl-, ethyl-, n-propyl-, n-butyl-, n-pentyl group.

The compounds of the general formula (I) produced by the invention are named after the nomenclature for prostaglandins and prostacycline analogs proposed by N. A. Nelson et. al. (N. A. Nelson, J. Med. Chem., 17, 911 (1974) and R. A. Johnson et al., Prostaglandins, 15, 737 (1978)).

The most fundamental compound in which the exo-enol ether moiety of $PGI_2$ has been converted to the inter-m-phenylene moiety is represented by the following formula:

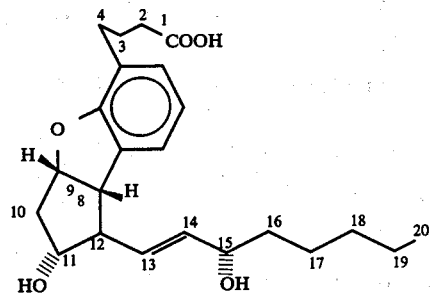

and after numbering each carbon atom as shown above, the compound is named as 5,6,7-trinor-4,8-inter-m-phenylene $PGI_2$.

Following the above-mentioned nomenclature, one of the compounds included in the present invention and represented by the following formula (II):

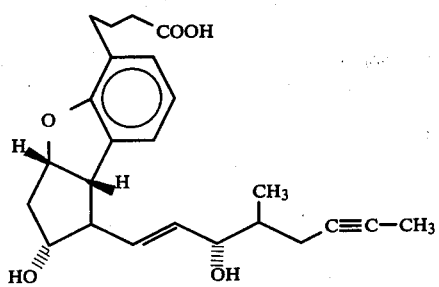

(II)

is named as 16-methyl-18,19-tetradehydro-5,6,7-trinor-4,8-inter-m-phenylene $PGI_2$.

Alternatively, the compound of the formula (II) may be named as a derivative of butyric acid by the more formal nomenclature. In such a case, the condensed ring moiety is named after the fundamental structure of 1H-cyclopenta[b]benzofuran of the following formula:

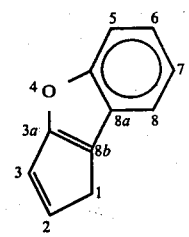

Accordingly, the formal name of the compound of the formula (II) is given as 4-[2-endo-hydroxy-1-exo-(3-hydroxy-4-methyl-6,7-tetradehydro-1-octenyl)-3a,8b-cis-2,3,3a,8b-tetrahydro-1H-5-cyclopenta[b]benzofuranyl]butyric acid.

In this specification, the structural formula of the compound of this invention is indicated only by one of a pair of optical isomers. It is, however, noticed that the compounds of the aforementioned general formula (I) are intended to include d-isomer, l-isomer and racemates. In addition, the RS representation showing the absolute configuration of the compound is omitted herein.

The compounds represented by the general formula (I) are exemplified as follows, but these illustrations are not to be construed as limiting the invention.

16-Methyl-18,19-tetradehydro-5,6,7-trinor-4,8-inter-m-phenylene $PGI_2$ (I)
16-Methyl-18,19-tetradehydro-5,6,7-trinor-4,8-inter-m-phenylene $PGI_2$ methyl ester (II)
18,19-Tetradehydro-5,6,7-trinor-4,8-inter-m-phenylene $PGI_2$ (III)
18,19-Tetradehydro-5,6,7-trinor-4,8-inter-m-phenylene $PGI_2$ methyl ester (IV)
20-Methyl-18,19-tetradehydro-5,6,7-trinor-4,8-inter-m-phenylene $PGI_2$ (V)
20-Methyl-18,19-tetradehydro-5,6,7-trinor-4,8-inter-m-phenylene $PGI_2$ methyl ester (VI)
16,20-Dimethyl-18,19-tetradehydro-5,6,7-trinor-4,8-inter-m-phenylene $PGI_2$ (VII)
16,20-Dimethyl-18,19-tetradehydro-5,6,7-trinor-4,8-inter-m-phenylene $PGI_2$ methyl ester (VIII)
20-Ethyl-16-methyl-18,19-tetradehydro-5,6,7-trinor-4,8-inter-m-phenylene $PGI_2$ (IX)
20-Ethyl-16-methyl-18,19-tetradehydro-5,6,7-trinor-4,8-inter-m-phenylene $PGI_2$ methyl ester (X)
16-Methyl-2,3-didehydro-18,19-tetradehydro-5,6,7-trinor-4,8-inter-m-phenylene $PGI_2$ (XI)
16-Methyl-2,3-didehydro-18,19-tetradehydro-5,6,7-trinor-4,8-inter-m-phenylene $PGI_2$ methyl ester (XII)
2,3-Didehydro-18,19-tetradehydro-5,6,7-trinor-4,8-inter-m-phenylene $PGI_2$ (XIII)
16-Methyl-13,14-dihydro-18,19-tetradehydro-5,6,7-trinor-4,8-inter-m-phenylene $PGI_2$ (XIV)
16-Methyl-13,14-dihydro-18,19-tetradehydro-5,6,7-trinor-4,8-inter-m-phenylene $PGI_2$ methyl ester (XV)
20-Methyl-19,20-tetradehydro-5,6,7-trinor-4,8-inter-m-phenylene $PGI_2$ (XVI)
17,18-Tetradehydro-5,6,7-trinor-4,8-inter-m-phenylene $PGI_2$ (XVII)

Among the compounds of the invention, those in which A is the group of —$CH_2$—$CH_2$—, $R^2$ and $R^3$ are hydrogen and X is the group of trans —CH=CH— may be produced by the following Reaction Scheme A.
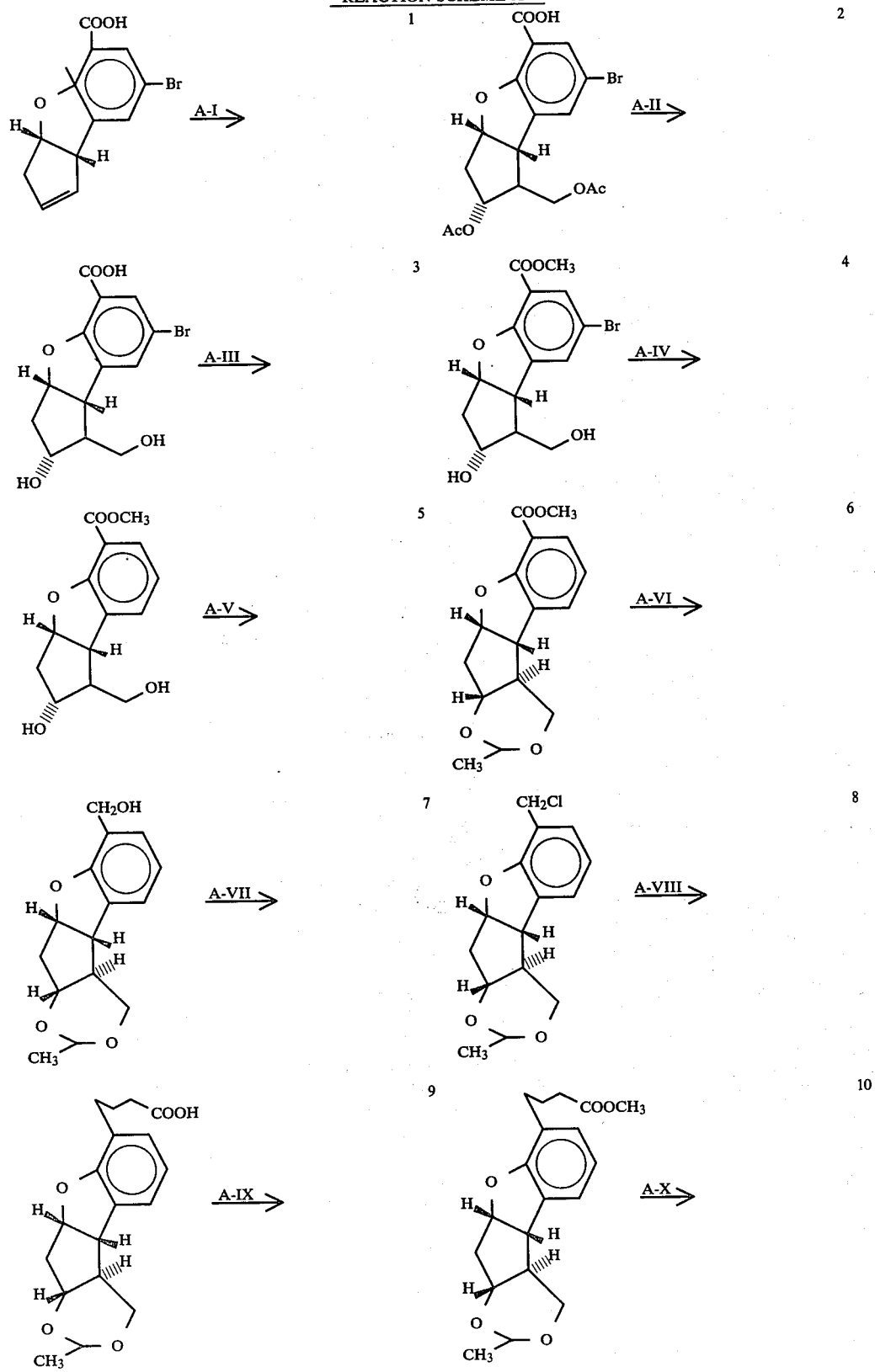
REACTION SCHEME A -continued
REACTION SCHEME A

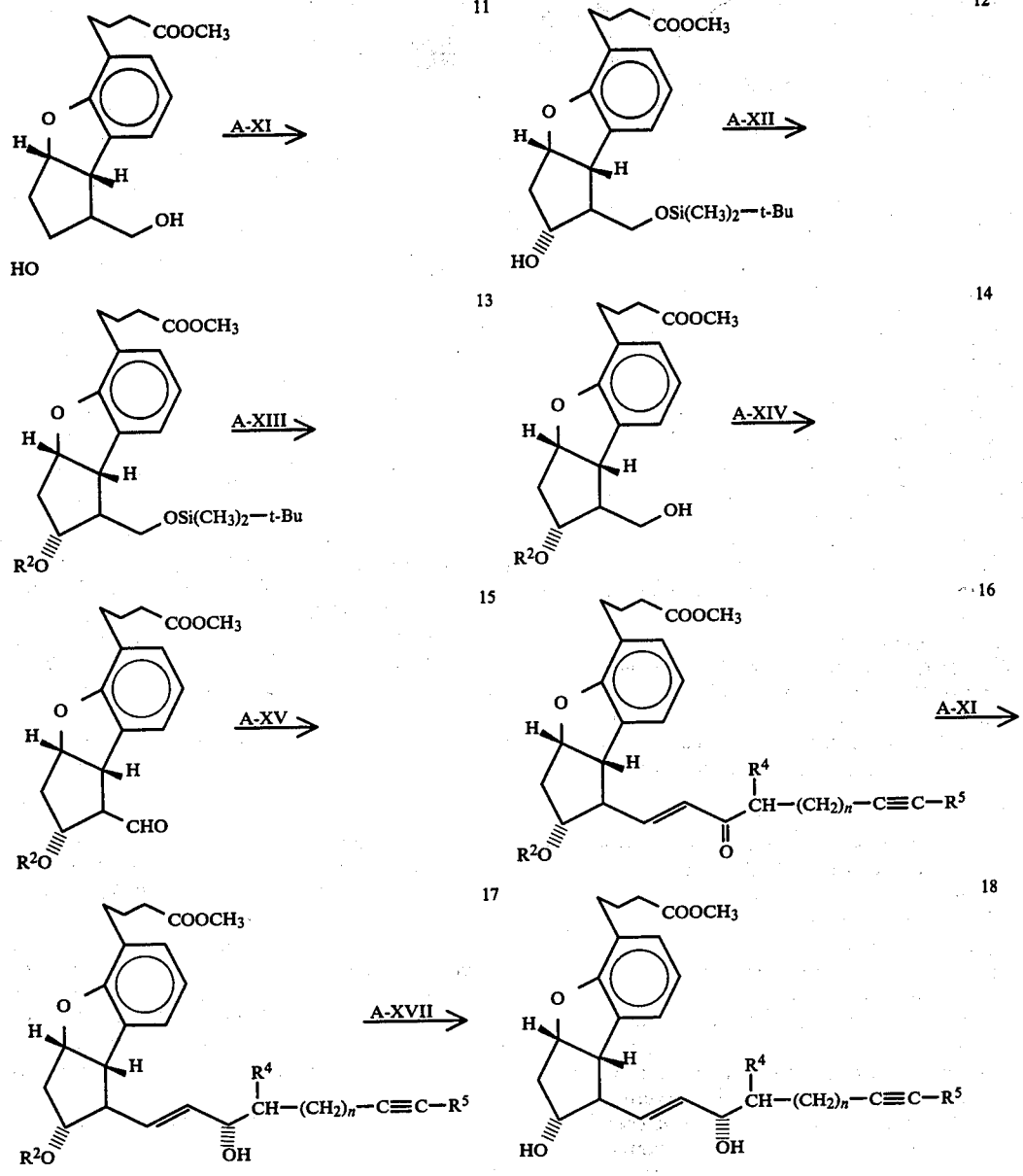

The starting material of bromocarboxylic acid, Compound 1, and the process for the preparation thereof are disclosed in Japanese Patent Application No. 29637/81.

The step A-I represents the conversion of Compound 1 to Compound 2 by the so-called Prins reaction and is ordinarily proceeded by heating bromocarboxylic acid 1 and formalin or a compound equivalent to the formalin in the solvent of acetic acid under the presence of an acid catalyst. As the compound equivalent to the formalin, paraformaldehyde and 1,3,5-trioxane may be mentioned. As the catalyst, sulfuric acid, chlorosulfonic acid, trifluoroacetic acid, perchloric acid, phosphoric acid, etc. may be mentioned, and the sulfuric acid is preferably used. The reaction is carried out at a temperature in the range from an ambient temperature to 200° C. and ordinarily the favorable reaction rate is available at a temperature in the range from 60° to 90° C. After the solvent and the solid derived from the formaldehyde were removed from the reaction system, the product 2 is used as a starting material without further purification.

The step A-II is a step for hydrolysis of the ester group of Compound 2, which can be conducted by adding to a solution of the Compound 2 in methanol or ethanol an aqueous solution of sodium hydroxide, potassium hydroxide, sodium carbonate or potassium carbonate in an amount more than 3 equivalent amount. The reaction is carried out at a temperature from 0° to 150° C., and is preferably from 20° to 100° C. to give a preferred reaction rate. After the solvent is removed, water is added to the residue and the mixture is acidified (pH 2-4) and extracted with organic solvent not miscible with water such as ethyl acetate, ether, chloroform, dichloromethane etc. to give a crude crystal 3. The organic solvent for the extraction is not restricted to the above-mentioned.

Compound 3 is used in the next step as the starting material without purification.

The step A-III is a step of conversion of the carboxylic acid obtained in step A-II into the corresponding methyl ester, which can be carried out by addition of an amount of more than stoichiometrical amount of a solution of diazomethane in ether to a solution of 3 in a solvent at a temperature from −20° to 40° C. The reaction proceeds instantaneously to afford Compound 4. As another method for carrying out step A-III, for instance, a method wherein Compound 3 is methylated with methyl iodide in acetone in the presence of potassium carbonate and a method wherein Compound 3 is heated with methanol in the presence of an acid catalyst, preferably p-toluenesulfonic acid, sulfuric acid, alkylsulfate, acidic ion-exchanging resin or phosphoric acid, in benzene or toluene followed by removing water formed during the reaction may be mentioned. For more in detail, refer to J. F. W. McOmie "Protective Groups in Organic Chemistry", pages 183 to 210(1973) by Plenum Press, S. R. Sandler and W. Karo "Organic Functional Group Preparations", pages 245 to 265(1968) by Academic Press or C. A. Buehler and D. E. Pearson "Survey of Organic Syntheses" Chapt. 14, pages 802 to 825, Wiley-Interscience Ed. The usual methods of esterification shown in these references are applicable to step A-III.

The step A-IV is a step for the dehalogenation of Compound 4 and carried out by the so-called hydrogenation. More in detail, the step is completed by effecting the reaction under a pressure of hydrogen (from an ordinary pressure to 10 atm) in the presence of a catalyst such as palladium-carbon, palladium-barium sulfate, Raney-nickel, etc. It is preferable to effect the reaction in the presence of a neutralizing agent such as sodium carbonate, potassium carbonate, sodium acetate, potassium acetate, etc. for the purpose of neutralizing hydrogen bromide formed in the reaction.

The step A-V is a step for conversion of the diol in Compound 5 into the acetal of acetaldehyde, Compound 6. For that purpose, Compound 5 is dissolved into a solvent together with acetaldehyde, 1,1-dimethoxyethane or 1,1-diethoxyethane, and after an acid is added to the solution, the mixture is heated at a temperature from 0° to 150° C., preferably at a temperature from 40° to 100° C. to cause reaction. As the solvent, an aprotic solvent such as tetrahydrofuran, dimethoxyethane, dioxane, benzene, toluene, dimethylformamide, ether, ethyl acetate, dichloromethane, chloroform, trichloroethylene and the like may be mentioned, and tetrahydrofuran is preferable. As the acid, p-toluenesulfornic acid, phosphoric acid, sulfuric acid, acidic ion-exchanging resin or trifuloroacetic acid may be mentioned, and the use of p-toluenesulfonic acid gives a satisfactory result.

The step A-VI is a reduction step for converting the acetal 6 to the corresponding alcohol 7. As the reducing agent, lithium aluminum hydride and hydrogen in the presence of a Cu-Cr catalyst may be mentioned, and lithium aluminum hydride is preferable.

The step A-VII is the conversion step of the alcohol 7 to the corresponding chloride, wherein the Compound 7 is treated with thionyl chloride in an organic solvent in the presence of a base. As the base, although pyridine is preferably used, a tertiary amine may be used. Instead of thionyl chloride, phosphorous trichloride, triphenylphosphine-$CCl_4$, phosphorous oxychloride and the like may be used in the step A-VII.

The step A-VIII is the conversion step of the halide 8 into a carboxylic acid 9 having three elongated carbons. The step is carried out by converting the chloride in Compound 8 to the corresponding Grignard reagent and adding β-propiolactone to the Gringnard reagent in the presence of a copper catalyst.

Though cuprous iodide is preferable as the copper catalyst, other monovalent copper compound such as cuprous chloride, cuprous bromide, tributylphosphinpentyn(1)yl-copper(I) may be used in this step.

The step A-IX is the conversion step of the carboxylic acid 9 to the corresponding methyl ester 10. The step is carried out substantially in a similar manner as in the step A-III.

The step X is a step for the solvolysis of the cyclic acetal in Compound 10 to give a diol, wherein the solvolysis is effected by the addition of an acid to a solution of Compound 10. The solvent is exemplified by methanol, ethanol, aqueous methanol, aqueous ethanol, isopropyl alcohol, butanol. The acid catalyst is exemplified by hydrochloric acid, sulfuric acid, phosphoric acid, p-toluenesulfonic acid, trifluoroacetic acid, acidic ion-exchanging resin, acetic acid, etc., however, not being restricted thereto. The hydrochloric acid ordinarily gives a sufficiently desirable result. The reaction temperature is in the range from −20° to 200° C., and is preferably from 0° to 70° C.

The step A-XI is a step for selective protection of the primary hydroxyl group in diol 11 using dimethyl-t-butylsilylchloride. In this step, imidazole is preferably used as a base.

The step A-XII is a step for esterification of the remaining free hydroxyl group of Compound 12, in which Compound 12 is reacted with an acyl- or aroyl halide represented by the formula of $R^2Y$ wherein $R^2$ is the same as has been defined hereinbefore but excepting a hydrogen atom and Y is an atom of chlorine, bromine or iodine, or an acid anhydride represented by the formula $R^2$—O—$R^2$ wherein $R^2$ is the same as has been defined before but excepting a hydrogen atom.

Examples of the acyl- and aroyl halide include acetyl chloride, propionyl chloride, butyroyl chloride, acetyl iodide, decanoyl chloride, benzoyl chloride, p-toluoyl chloride, p-phenylbenzoyl chloride, etc. The acyl- and aroyl halide is, however, not restricted to these illustrations.

Examples of the acid anhydride include acetic anhydride, propionic anhydride, butyric anhydride, benzoic anhydride, etc. The acid anhydride is, however, not restricted to these illustrations.

The reaction of step A-XII may be carried out in the coexistence of an acid or a base. Particularly, in the condensation of $R^2Y$ and the alcohol of Compound 12, the base, for instance, pyridine or a tertiary amine such as triethylamine is coexisted as a catalyst. The condensation reaction of the alcohol 12 with the acid anhydride may be carried out by heating a mixture in the presence or absence of the acid or the base. As the acid, sulfuric acid, phosphoric acid, acidic ion-exchanging resin or boron trifluoride is preferably used, and as the bases, pyridine, an analogous compound such as p-dimethylaminopyridine or a tertiary amine such as triethylamine is preferably used. Ordinarily, the pyridine is preferably used and it serves as the base and also as the solvent. In the reaction, solvent may be or may not be used. In using a solvent, an aprotic one is used, for instance, tetrahydrofuran, dimethoxyethane, benzene, toluene, ether, dimethylformamide, dioxane, etc.

The step A-XIII is a step for removing the dimethyl-t-butylsilyl group in Compound 13 to obtain Compound 14. The reaction is effected by leaving a solution of Compound 13 in an aqueous solution of acetic acid to stand for 0.5 to 48 hours at a temperature from 15° to 100° C. Alternatively, the compound 13 may be treated with quarternary ammonium fluoride in an organic solvent. The examples of the quaternary ammonium fluoride are tributylammonium fluoride, trioctylammonium fluoride and the like but not restricted thereto.

The step A-XIV is a step for oxidation of the alcohol 14 to give an aldehyde 15. Although various oxidizing agent have been known for the oxidization, chromic anhydride-pyridine complex (Collins' reagent), dimethylsulfoxide dicyclohexylcarbodiimide, dimethylsulfide-chlorine and a base, dimethylsulfide N-bromosuccinic imide or the like are particularly preferable.

The step A-XV is a step for reaction of the aldehyde 15 with a sodium salt of dialkylphosphonic acid ester of the formula:

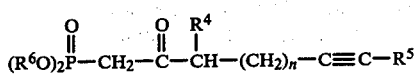

wherein $R^4$, $R^5$ and n are the same as has been defined above and $R^6$ is an alkyl group such as methyl, ethyl, propyl, octyl, etc., in an organic solvent to afford Compound 16. The examples of the solvent are an ether such as tetrahydrofuran and dimethoxyethane and the solvent used in Wittig's reaction, for instance, dimethylsulfoxide, dialkylformamide and the like.

The dialkylphosphonic acid ester may be easily synthesized according to the following reaction (E. J. Corey et al., J. Am. Chem. Soc., 88, 5654(1966)):

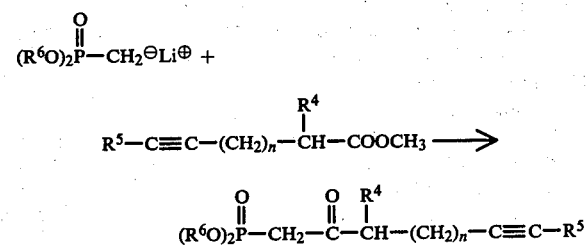

wherein $R^4$, $R^5$, $R^6$ and n are the same as has been defined above.

The step A-XVI is a reduction step of α,β-unsaturated ketone to afford allyl alcohol. The reducing agent is preferably zinc borohydride, $Zn(BH_4)_2$. Other nonlimitative examples of the reducing agent are cerium chloride/sodium boronhydride($NaBH_4$), lithium aluminum hydride ($LiAlH_4$)/α,α'-binaphthol, diisobutylalumium(2,6-dimethylphenoxide), aluminum triisopropoxide and the like.

The reduction product in this step A-XVI contains a mixture of the 15-α-isomer and the 15-β-isomer, and the mixture is used in the next step A-XVII without purification. The necessary product, 15-α-isomer may be isolated by column chromatography after the next step A-XVII.

The step of A-XVII is a step for ester exchange of Compound 17. The step is carried out by dissolving Compound 17 in methanol and adding a base such as anhydrous potassium carbonate and sodium methoxide as a catalyst to the solution.

Among the compounds of the invention, those in which A is $-CH_2-CH_2-$, $R^1$, $R^2$ and $R^3$ are respectively a hydrogen atom may be prepared according to the following Reaction Scheme B.

REACTION SCHEME B

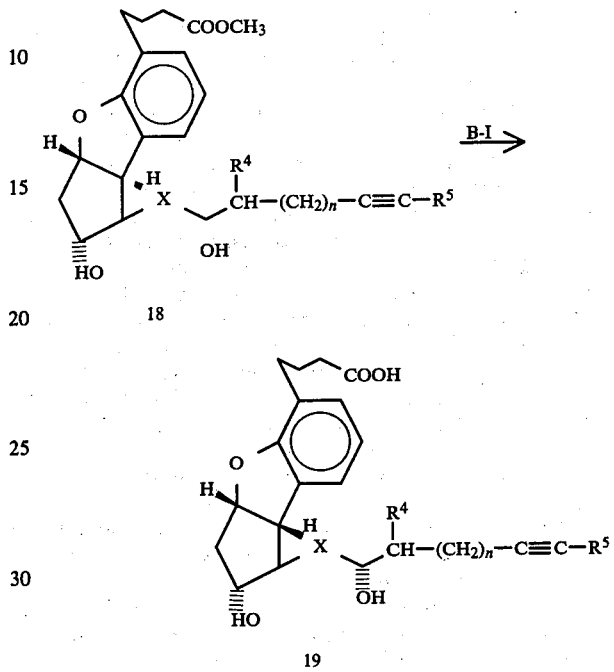

The step B-I is a step for hydrolysis of the methyl ester 18 to afford a free carboxylic acid 19. This hydrolysis is carried out by dissolving Compound 18 in methanol or ethanol and after adding an aqueous solution containing more than the stoichiometric amount of a base such as sodium hydroxide, potassium hydroxide, sodium carbonate or potassium carbonate to the alcoholic solution, heating the mixture at a temperature from 0° to 150° C., preferably 20° to 60° C. The base is not necessarily restricted to the above-mentioned bases, and the solvent of aqueous tetrahydrofuran, aqueous dioxane, aqueous dimethoxyethane, dimethylsulfoxide or the like may be used in stead of methanol or ethanol.

Among the compounds included in the present invention, those in which $R^1$, $R^2$ and $R^3$ are respectively a hydrogen atom and A is trans $-CH=CH-$ may be prepared according to the following Reaction Scheme C.

REACTION SCHEME C

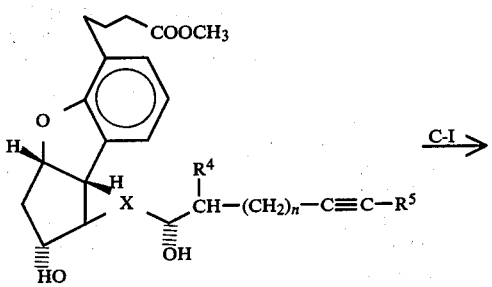

-continued
REACTION SCHEME C

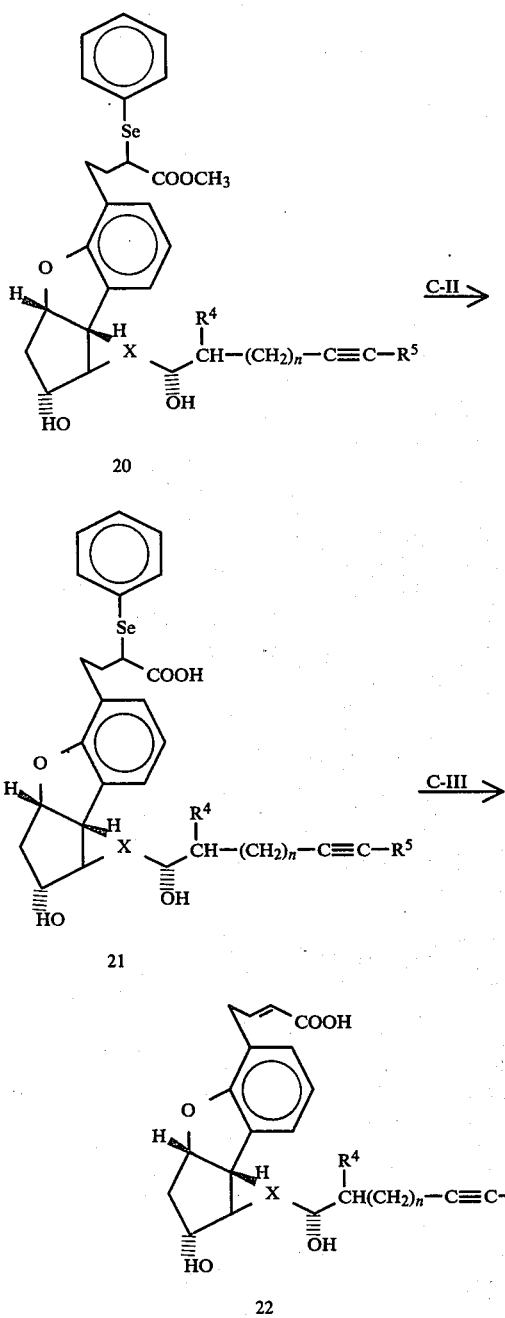

tants after the addition of diphenyl diselenide and to heat the mixture in the range from 0° to 60° C. for completing the reaction.

The step C-II is a step for hydrolysis of the methyl ester 20 to give a free carboxylic acid 21. The reaction may be carried out in a similar manner to that in the step B-I.

The step C-III is a step for removing the phenylseleno group in Compound 21. Ordinarily, for such a purpose, hydrogen peroxide is used. The hydrogen peroxide oxidizes the phenylseleno group followed by removing the group. An aqueous 30% by weight solution of hydrogen peroxide is used in excess in this step, and after the reaction is over, the excess was reduced by a reducing agent such as dimethyl sulfide, sodium thiosulfate, sodium hydrogen sulfite and the like.

Among the compounds included in the present invention, those in which $R^1$ is the normal alkyl group of 1 to 12 carbon atoms are prepared by the following Reaction Scheme D.

REACTION SCHEME D

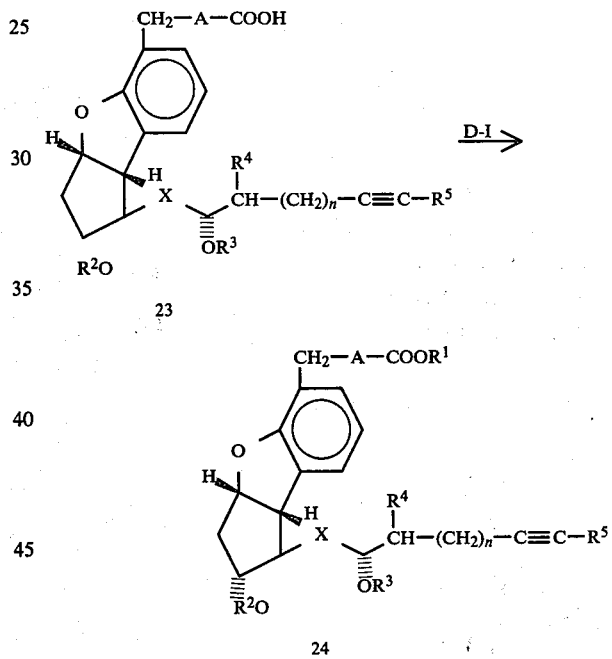

The step C-I is a reaction step wherein a hydrogen atom attached to the carbon atom at alpha position of the carbonyl carbon atom of the methoxycarbonyl group of Compound 18 is substituted by a phenylseleno group. The substitution is carried out by bringing 3 to 3.5 equivalent amount of diisopropylaminolithium into reaction with one equivalent amount of Compound 18 at a low temperature from −80° to −40° C. and adding diphenyl diselenide to the mixture in an organic solvent, most preferably in tetrahydrofuran. The solvent is not necessarily limited to tetrahydrofuran. It is preferable to add hexamethylphosphonic triamide (HMPt) to the reaction system for raising the reactivity of the reac- The step D-I is a step for the esterification of a carboxylic acid. In general, when a solution of diazoalkane in ether is added to a solution of Compound 23 in an organic solvent, the esterification proceeds instantly with the evolution of gaseous nitrogen. The non-limitative examples of diazoalkane are diazomethane, diazoethane, diazo-n-propane, diazo-n-butane, diazo-n-dodecane and the like. Other methods for the esterification may be preferably applicable wherein Compound 23 is at first converted to sodium salt or a salt of a tertiary amine and ethyl chlorocarbonate is added to form a mixed acid anhydride in the reaction system, and then an alcohol, $R^1OH$ wherein $R^1$ is a normal alkyl of 1 to 12 carbon atoms is added to the system and the system is heated.

Among the compounds of the invention, those in which $R^2$ and $R^3$ are the same acyl or aroyl group may be prepared by the following Reaction Scheme E.

REACTION SCHEME E

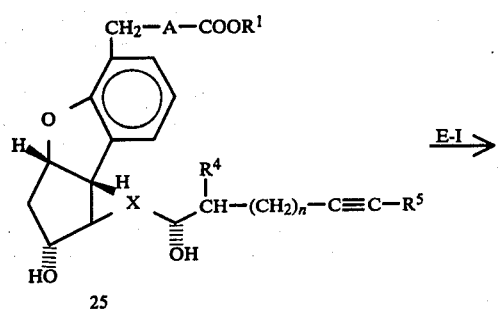

25

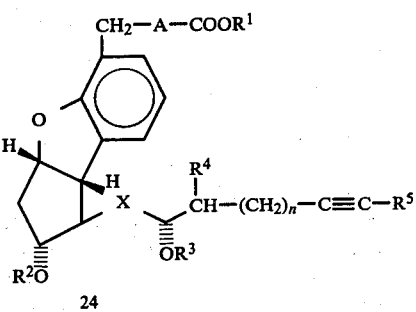

24

The step E-I may be proceeded as in the step A-XII.

Among the compounds of the invention, those in which X is —$CH_2$—$CH_2$—, $R^1$ is the methyl group and A is —$CH_2$—$CH_2$— may be prepared by the following Reaction Scheme F.

REACTION SCHEME F

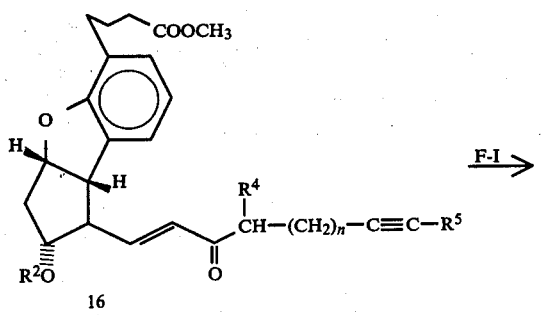

16

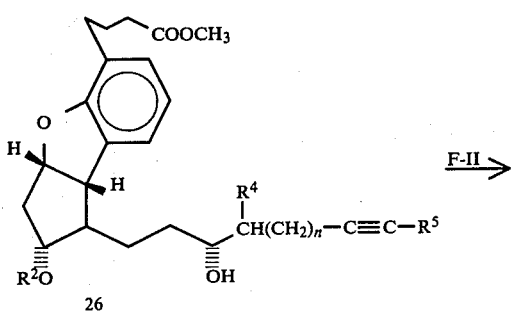

26

-continued
REACTION SCHEME F

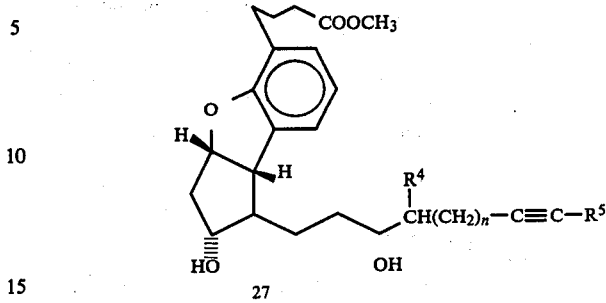

27

The step F-I is a simultaneous reduction step of a double bond between the carbon atoms of positions 13 and 14 of Compound 16 and a carbonyl group adjacent to the double bond. In the step, sodium borohydride ($NaBH_4$) is added as a reducing agent to a solution of Compound 16 in pyridine to carry out the reaction.

The step F-II may be carried out as in the Step A-XVII.

Among the compounds of the invention, those compounds in which X is —$CH_2$—$CH_2$— may be generally prepared by carrying out the suitable reactions shown in each step of Reaction Schemes B, C, D and E while using Compound 27 as the starting compound.

Any one of Reaction Schemes A to F may be applied for producing the d-isomer, the l-isomer and the racemates compound of the compound according to the present invention. The optical isomer of the compound can be obtained from the optically active product resolved, for instance, in Reference Example 20 or 21 hereinafter mentioned.

The compounds within the present invention have potent platelet aggregation inhibiting activity and blood pressure decreasing activity by vasodilating action. Furthermore, the compounds have the potent gastric mucosa protecting action and potent gastric juice secretion inhibiting action.

According to Born's method (Nature, 194, 927(1962)), the efficacy of the compound to inhibit platelet aggregation was examined. The blood was collected from human or anesthetized rabbits. The blood was anti-coagulated with a 3.8% aqueous solution of sodium citrate in an amount of a tenth volume of the blood and was centrifuged for 10 minutes at 200×g to obtain platelet rich plasma. After pretreatment with the compound of the invention to the platelet rich plasma aggregation was measured by aggregometer with arachidonic acid, adenosine-2-phosphate(ADP) or collagen as aggregation inducer. It was shown that compound (I), (III), (VII) and (XI) had the same or more potent inhibitory activity than prostaglandin $E_1$. It should be noted that the compound (I) [$ED_{50}$0.7 ng/ml] or (III) [$ED_{50}$8 ng/ml] exhibit more potent human platelet aggregation inhibiting activity induced by ADP than the corresponding $C_{18}$, $C_{19}$-Saturated compounds, 16-methyl-5,6,7-trinor-4,8-inter-m-phenylene $PGI_2$ [$ED_{50}$15 ng/ml] or 5,6,7-trinor-4,8-inter-m-phenylene $PGI_2$ [$ED_{50}$ 19 ng/ml] respectively.

To examine the efficacy of the compound to reduce the blood pressure, the blood pressure of carotid artery of rats under pentobarbital anesthesia was measured. The compounds (I), (III), (VII) and (XI) were injected into the vein through indwelling catheter. These compounds of the invention exhibited the same activity as prostaglandin E$_1$ at the same dose of 0.05 to 100 μg/kg, but compounds (I), (III), (VII) and (XI) had the longer duration than prostaglandin E$_1$.

According to the method of Robert et al. (Gastroentrology, 77, 433(1979)), the activity of compounds (I), (III), (VII) and (XI) to protect the gastric mucosal membrane was examined. The compounds efficiently suppressed the lesions caused by ethanol on the gastric mucosa of rats by oral administration at the dose of 10 to 30 μg/kg, which is 0.3 to 1 time of the equipotent dose of prostaglandin E$_2$.

According to Shay's method (Gastroenterology, 26, 906 (1954)), the activity of the compounds in the present invention to suppress the secretion of gastric juice was examined. Compound VII significantly suppressed the secretion of gastric juice by subcutaneous injection in a dose of 0.3 to 1 mg/kg which corresponds to 0.1 to 0.3 times of the equipotent dose of prostaglandin E$_2$. The compounds of the invention, particularly Coumpounds I, III, VII and XI showed no symptoms of diarrhea in rats even up to the dose of 3 mg/kg by subcutaneous administration.

Therefore, the compound of this invention may be used as medicine for an anti-peptic ulcer agent, an anti-thrombotic agent and a blood pressure-reducing agent. In addition, the compounds may also be applied to an anti-asthmatic agent because of their relaxing activity of the tracheal smooth muscle.

The anti-thrombotic agent containing the compounds of the present invention as an active component may be applied to extracorporeal circulation, treatment of the disturbance of peripheral circulation such as Buerger's disease and Raynaud's disease, prevention and treatment of myocardial infarction, angina pectoris and cerebral infarction, prevention of TIA, treatment of diabetic thrombosis and prevention and treatment of arterioscrelosis.

For the treatment of gastric ulcer, the subject compound is administered in a pharmaceutically effective amount of 0.01 to 100 mg/person one to three times a day orally, subcutaneously, intramuscularly or intrarectally. For the treatment of Buerger's disease, the pharmacologically effective intravenous dose of the subject compound amouns 0.001 to 100 μg/kg/min. In case of using the subject compound as the anti-thrombotic agent, 0.001 to 50 mg of the compound is orally administered per person one to three times a day, and in case of using the subject compound as the blood pressure-reducing agent, 0.01 to 50 mg of the compound is orally administrated per person one to three times a day.

The compound according to the present invention can be orally administered as a form of solid substance containing an excipient such as starch, lactose, sucrose, a certain kind of clay and a seasoning agent, or can be parenterally administered in a form of a sterilized aqueous solution. Such a solution may contain another solute, for instance, glucose or sodium chloride in an amount sufficient for making the solution isotonic. Since the compound has a considerable stability due to the chemical structure thereof, there is no difficulty in manufacturing the preparation. Therefore, various preparations for oral administration, injections and suppositories can be prepared.

The present invention will be explained more in detail while referring to the following examples and reference examples.

REFERENCE EXAMPLE 1

Methyl 2-endo-hydroxy-1-exo-hydroxymethyl-3a,8b-cis-2,3,3a,8b-tetrahydro-1H-5-cyclopenta[b]benzofurancarboxylate

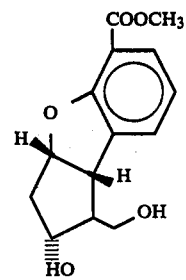

To a suspension of 4 g of trioxane in 28 ml of acetic acid was added 1.2 ml of concentrated sulfuric aicd, and the mixture was heated to 80° C. with stirring. To the solution was added in small portions 2 g of 7-bromo-3a,8b-cis-3a,8b-dihydro-3H-5-cyclopenta[b]benzofurancarboxylic acid. After being stirred at 80° C. for 14 hours, the reaction mixture was cooled, and the acetic acid was removed under reduced pressure.

The residue was subjected to azeotropic operation with toluene two times, and ether was added to the residue. The and the precitirate derived from trioxane was removed by filtration and washed with ether, and the combined ethereal solutions were concentrated under reduced pressure. The residue was dissolved in ethyl acetate, and the solution was washed with water and aqueous saturated solution of sodium chloride, was dried, and was concentrated to give 4 g of an oily material. The oily material was dissolved in 20 ml of methanol and to the solution was added 20 ml of aqueous 1N solution of sodium hydroxide, and the mixture was stirred for 14 hours at room temperature. After removal of methanol under reduced pressure, water was added to the mixture, and this solution was acidified to pH3 with aqueous 2N hydrochloric acid. The mixture was extracted five times with ethyl acetate, and the ethyl acetate extract was dried and concentrated to give 3.5 g of crude crystals. After addition of ethanol to the crude crystals, the crude crystals were filtered. The filtrate was concentrated, and to the residue was added ethanol and ethyl acetate, and precipitate was collected by filtration. The combined amount of the crude crystals was 1.6 g.

After the combined crude crystals were methylated with diazomethane, the reaction product was dissolved in 20 ml of ethyl acetate. To this solution was added 1.5 g of sodium acetate and 300 mg of 10% palladium-carbon, and the mixture was stirred for 2 hours under hydrogen. Then, the reaction product was filtered, and after addition of aqueous saturated solution of sodium hydrogen carbonate to the filtrate, the mixture was extracted two times with ethyl acetate.

The extract was washed with an aqueous saturated solution of sodium chloride, dried, and concentrated to give 1.3 g of crude crystals. The crude crystals were recrystallized from ethyl acetate to yield 765 mg of the captioned compound (melting point; 134° to 135° C., yield; 43%).

IR spectrum(KBr) ν: 3400, 1715, 1605 and 760 cm$^{-1}$

NMR spectrum(in CDCl₃) δ: 1.50 to 2.80 (5H), 3.50 (1H, t J=7.0 Hz), 3.80 (2H, m), 3.90 (3H, s), 4.12 (1H, q, J=6.0 Hz), 5.30 (1H, m), 6.90 (1H, t, J=8.0 Hz), 7.14 (1H, d, J=8.0 Hz), and 7.74 (1H, d, J=8.0 Hz)

|  |  | C | H |
|---|---|---|---|
| Mass spectrum (m/e): | 2.64(M⁺) | | |
| Elementary analysis: | Calculated as C₁₄H₁₆O₅ | 63.62 | 6.10 |
| | Found | 63.36 | 6.20 |

REFERENCE EXAMPLE 2

Methyl 3-methyl-trans-4a-cisoid-4a,5a-cis-5a-1,4a,5,5a,10b,10c-hexahydro-7-dioxino[5,4-a]cyclopenta[b]benzofuran-carboxylate

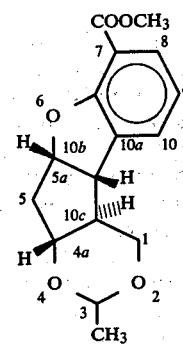

To a stirred suspension of 3 g of methyl 2-endo-hydroxy-1-exo-hydroxymethyl-3a,8b-cis-2,3,3a,8b-tetrahydro-1H-5-cyclopenta[b]benzofurancarboxylate in 30 ml of anhydrous tetrahydrofuran was added 1.5 ml of a solution which is obtained by dissolving 10 ml of 1,1-diethoxyethane and 200 mg of p-toluenesulfonic acid mono-hydrate into 10 ml of tetrahydrofuran followed by drying over molecular sieves, and the mixture was stirred for 14 hours at 60° C. and then cooled.

To the reaction mixture was added 100 mg of sodium hydrogen carbonate, and the mixture was stirred for 10 min at room temperature. Then, water was added to the reaction mixture and the mixture was extracted three times with ethyl acetate. The combined organic layers were washed with water and aqueous saturated solution of sodium chloride, was dried, and was concentrated to give 3.5 g of the crude crystals. The crude crystals were recrystallized from benzene-hexane to yield 2 g of the titled compound (m.p. 162°–163° C.).

The filtrate was concentrated and the residue was dissolved again in 10 ml of anhydrous tetrahydrofuran. To this solution were added 2.5 ml of 1,1-diethoxyethane and 1 ml of the above-mentioned solution of p-toluenesulfonic acid monohydrate in tetrahydrofuran and the mixture was stirred for 14 hours at 60° C. and then cooled. To the reaction mixture was added 100 mg of sodium hydrogen carbonate, and the mixture was stirred for 10 min at a room temperature. After addition of water, the mixture was extracted three times with ethyl acetate. The combined organic layers were washed with water and aqueous saturated solution of sodium chloride, dried, and concentrated to give 1.5 g of crude crystals. The crude crystals were recrystallized from benzene-hexane to yield 740 mg of the captioned compound (m.p. 154°–156° C., yield 83%).

IR spectrum(KBr) ν: 1715, 1607, 1210 and 755 cm⁻¹

NMR(CDCl₃) δ: 1.36 (3H, d, J=5.0 Hz), 2.00 (2H, m), 2.80 (1H, m), 3.40 (2H, m), 3.72 (1H, t, J=10.0 Hz), 3.90 (3H, s), 4.40 (1H, dd, J=10.0 Hz), 4.74 (1H, q, J=4.0 Hz), 5.30 (1H, m), 6.89 (1H, t, J=8.0 Hz), 7.26 (1H, dd, J=8.0 and 2.0 Hz) and 7.80 (1H, dd, J=8.0 and 2.0 Hz)

Mass spectrum(m/e): 290 (M⁺) and 259 (-31)

REFERENCE EXAMPLE 3

3-methyl-trans-4a-cosoid-4a,5a-cis-5a-1,4a,5,5a,10b,10c-hexahydro-7-dioxino[5,4-a]cyclopenta[b]benzofuranyl-methanol To a suspension of 1 g of lithium aluminum hydride in 10 ml of anhydrous tetrahydrofuran cooled in an ice bath was added dropwise a solution of 1.94 g of methyl 3-methyl-trans-4a-cisoid-4a,5a-cis-5a-1,4a,5,5a,10b,10c-hexahydro-7-dioxino[5,4-a]cyclopenta[b]-benzofuran-carboxylate in 40 ml of anhydrous tetrahydrofuran. After being stirred for 30 min at room temperature, the reaction mixture was cooled in an ice bath. The excess of lithium aluminum hydride was decomposed by the addition of ethyl acetate, and aqueous saturated solution of potassium sodium tartarate was added to the reaction mixture. After filtration of the mixture, the filtrate was concentrated and the residue was dissolved in 10 ml of methanol. After addition of 2 g of potassium carbonate to the solution, the mixture was stirred for 3 hours at room temperature and was concentrated. After water was added to the residue, the aqueous mixture was extracted 3 times with ethyl acetate. The combined organic layers were washed with water and saturated aqueous solution of sodium chloride, dried, and concentrated to give 2 g of crude crystals. The crude crystals were recrystallized from ethyl acetate-hexane to yield 1.49 g of the pure crystals (m.p.; 124° to 125° C. yield; 85%).

IR(KBr) ν: 3305, 1595, 1155, 1015 and 745 cm⁻¹

NMR(CDCl₃) δ: 1.36 (3H, d, J=5.0 Hz), 2.00 (2H, m), 2.72 (1H, m), 3.38 (2H, m), 3.70 (1H, t, J=10.0 Hz), 4.40 (1H, dd, J=10.0 Hz and 4.0 Hz), 4.70 (3H, m), 5.08 (1H, m), 6.82 (1H, t, J=7.5 Hz), 7.04 (1H, dd, J=7.5 Hz and 1.5 Hz), 7.14 (1H, dd, J=7.5 Hz and 1.5 Hz)

Mass(m/e): 262 (M⁺) and 229 (-33)

REFERENCE EXAMPLE 4

7-chloromethyl-3-methyl-trans-4a-cisoid-4a,5a-cis-5a-1,4a,5,5a,10b,10c-hexahydrodioxino[5,4-a]cyclopenta[b]benzofuran

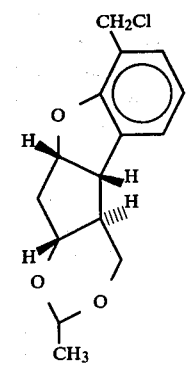

To a solution of 1.14 g of 3-methyl-trans-4a-cisoid-4a,5a-cis-5a-1,4a,5,5a,10b,10c-hexahydro-7-dioxino[5,4-a]cyclopenta[b]benzofuranylmethanol in 10 ml of dimethoxyethane cooled in an ice bath was added 0.43 ml of anhydrous pyridine and 0.38 ml of thionyl chloride, and the mixture was stirred for 3 hours at room temperature. After addition of ether to the reaction mixture, the precipitate was filtered, and water was added to the filtrate and the mixture was extracted three times with ether. The extract was washed with aqueous saturated solution of copper sulfate, water, aqueous saturated solution of sodium hydrogen carbonate and aqueous saturated solution of sodium chloride, dried, and concentrated to give 1.2 g of crude crystals. The crude crystals were recrystallized from ethyl acetate-hexane to yield 1 g of the pure chloride (m.p.; 94° to 95° C., yield; 83%).

IR(KBr) $\nu$: 1600 and 745 cm$^{-1}$

NMR(CDCl$_3$) $\delta$: 1.36 (3H, d, J=5.0 Hz), 2.00 (2H, m), 2.78 (1H, m), 3.38 (2H, m), 3.72 (1H, t, J=10.0 Hz), 4.40 (1H, dd, J=10.0 Hz and 4.0 Hz), 4.60 (2H, s), 4.72 (1H, q, J=5.0 Hz), 5.20 (1H, m), 6.83 (1H, t, J=7.0 Hz) and 7.10 (2H, m)

Mass(m/e): 280 and 282 (M+) and 245

REFERENCE EXAMPLE 5

4-[3-methyl-trans-4a-cisoid-4a,5a-cis-5a-1,4a,5,-5a,10b,10c-hexahydro-7-dioxino[5,4-a]cyclopenta[b]benzofuranyl]butyric acid

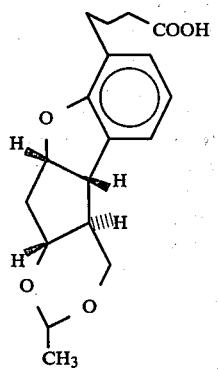

A solution of 482 mg of 7-chloromethyl-3-methyl-trans-4a-cisoid-4a,5a-cis-5a-1,4a,5,5a,10b,10c-hexahydrodioxino[5,4-a]cyclopenta[b]benzofuran in 5 ml of anhydrous tetrahydrofuran was added dropwise to 84 mg of turnings of metallic magnesium with stirring to prepare a Grignard reagent. To the thus prepared Grignard reagent cooled in an ice bath were added 30 mg of cuprous iodide and 0.1 ml of beta-propiolactone, and the mixture was stirred for one hour. Aqueous ammonium chloride solution was added to the reaction mixture, and the mixture was acidified with 1N hydrochloric acid to PH 3~4 to decompose the excess of magnesium. The resulting solution was extracted 5 times with ether, and the combined ethereal layers were washed with water and aqueous saturated solution of sodium chloride, dried and concentrated to give 500 mg of crude crystals. The crude crystals were recrystallized from ethyl acetate-hexane to yield 279 mg of the pure crystals of the carboxylic acid (melting point; 148° to 149° C., yield; 54%).

IR(KBr) $\nu$: 3600 to 2200, 1715, 1600 and 755 cm$^{-1}$

NMR(CDCl$_3$) $\delta$: 1.36 (3H, d, J=5.0 Hz), 1.95 (4H, m), 2.38 (2H, t, J=6.0 Hz), 2.64 (3H, m), 3.00 to 3.90 (3H, m), 4.40 (1H, dd, J=10.0 Hz and 4.0 Hz), 4.62 (1H, q, J=5.0 Hz), 5.10 (1H, m), 6.80 (1H, t, J=7.0 Hz) and 6.95 (3H, m)

Mass(m/e): 318 (M+)

|  | C (%) | H (%) |
| --- | --- | --- |
| Elementary analysis: Calculated as C$_{18}$H$_{22}$O$_5$ | 67.91 | 6.97 |
| Found | 67.93 | 7.14 |

REFERENCE EXAMPLE 6

Methyl 4-[2-endo-hydroxy-1-exo-hydroxymethyl-3a,8b-cis-2,3,3a,8b-tetrahydro-1H-5-cyclopenta[b]benzofuranyl]butyrate

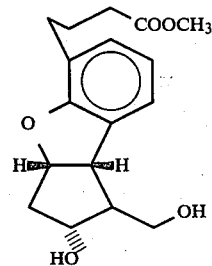

To a solution of 390 mg of 4-[3-methyl-trans-4a-cisoid-4a,5a-cis-5a-1,4a,5,5a,10b,10c-hexahydro-7-dioxino-[5,4-a]cyclopenta[b]benzofuranyl]butyric acid in 5 ml of ethyl acetate cooled in an ice bath was added an excess of an ethereal solution of diazomethane, and after being stirred for 5 min the mixture was concentrated. The resulting oily material was dissolved in 3 ml of methanol, and to the solution was added 1 ml of 1N hydrochloric acid and the mixture was stirred for 3 hours at room temperature. After concentration of the reaction mixture and addition of 1 ml of water, the mixture was extracted 3 times with each 5 ml of ethyl acetate. The combined layers of ethyl acetate were washed with 3 ml of water and 3 ml of aqueous saturated solution of sodium chloride, dried and concentrated to give 380 mg of crude crystals. The crude crystals were recrystallized from ethyl acetate-hexane to yield 200 mg of the pure captioned product (m.p.; 56° to 57° C., yield; 53%).

IR(KBr) $\nu$: 3400, 1737, 1595, 1255 and 745 cm$^{-1}$

NMR(CDCl$_3$) $\delta$: 1.70 to 2.90 (11H), 3.40 (1H, t, J=8.0 Hz), 3.65 (3H, s), 3.80 (2H, m), 4.10 (1H, q, J=7.0 Hz), 5.10 (1H, m), 6.80 (1H, t, J=7.0 Hz) and 7.00 (1H, m)

Mass(m/e): 306 (M+)

REFERENCE EXAMPLE 7

Methyl 4-[2-endo-acetoxy-1-exo-hydroxymethyl-3a,8b-cis-2,3,3a,8b-tetrahydro-1H-5-cyclopenta[b]benzofuranyl]butyrate To a solution of 350 mg of methyl 4-[2-endo-hydroxy-1-exo-hydroxymethyl-3a,8b-cis-2,3,3a,8b-tetrahydro-1H-5-cyclopenta[b]benzofranyl]butyrate in 3.5 ml of anhydrous dimethylformamide cooled in an ice bath were added 140 mg of imidazole and 360 mg of t-butyl-dimethylsilyl chloride, and after the mixture was stirred for 3 hours at room temperature, dimethylformamide was removed under reduced pressure. The residue was dissolved in a mixture of 10 ml of acetic anhydride and 5 ml of pyridine. After the mixture was stirred for 2 hours at room temperature, the reaction mixture was concentrated. Then the residual oil was dissolved in 5 ml of acetic acid, and to the solution were added 5 ml of tetrahydrofuran and 2 ml of water. After the mixture was stirred for 14 hours at 50° C. and concentrated, the residue was subjected to azeotropic operation two times with toluene. The residue was purified by column chromatography on silicagel using ethyl acetate-cyclohexane (1:2) to give 280 mg of the pure compound (yield; 70%).

IR(liquid film) $\nu$: 3450, 1740, 1595, 1240 and 745 cm$^{-1}$

NMR(CDCl$_3$) $\delta$: 1.82 (3H, s), 1.82 to 2.80 (10H), 3.66 (3H, s), 3.70 (3H, m), 5.00 to 5.35 (2H, m), 6.80 (3H, t, J=7.0 Hz) and 6.95 (2H, m)

Mass(m/e): 348 (M+)

REFERENCE EXAMPLE 8

Methyl ester of 11,15-dideoxy-11-acetoxy-16-methyl-15-oxo-18,19-tetradehydro-5,6,7-trinor-4,8-inter-m-phenylene PGI$_2$ In 1.4 ml of a solution of 0.3 ml of pyridine in 10 ml of benzene was dissolved 178 mg of methyl 4-[2-endo-acetoxy-1-exo-hydroxymethyl-3a,8b-cis-2,3,3a,8b-tetrahydro-1H-5-cyclopenta[b]benzofranyl]butyrate. To the solution were added 0.42 ml of the solution obtained by dissolving 0.14 ml of trifluoroacetic acid in 10 ml of dimethylsulfoxide and 320 mg of dicyclohexylcarbodiimide, and the mixture was stirred for 14 hours at room temperature. The precipitate was filtered and washed well with benzene. The filtrate was washed with water (3×3 ml), dried and concentrated to give 250 mg of crude aldehyde.

In the next step, 118 mg of sodium hydride (55% dispersion in mineral oil) was suspended in 20 ml of dimethoxyethane under argon. To the suspension was added a solution of 689 mg of dimethyl 3-methyl-2-oxo-hept-5-yne-phosphonate in 10 ml of dimethylformamide, and the mixture was stirred for 30 min at a room temperature.

To the thus prepared mixture was added a solution of 250 mg of the above-mentioned crude aldehyde in 5 ml of dimethoxyethane, and the mixture was stirred for 30 min at a room temperature. After neutralization (pH7) with acetic acid the mixture was concentrated. The residue was dissolved in 10 ml of pentane and ether (1:1), and the precipitate was filtered, and the filtrate was concentrated to give 800 mg of an oily material. The oily material was purified by column-chromatography using ethyl acetate and cyclohexane (1:3) as an eluent to yield 162 mg of the pure captioned product (yield; 70%).

IR(liquid film) $\nu$: 1740, 1700, 1670, 1630 and 1595 cm$^{-1}$

NMR(CDCl$_3$) $\delta$: 1.20 (3H, d, J=6.3 Hz), 1.78 (3H, t, J=3.1 Hz), 1.60 to 2.60 (12H), 3.67 (3H, s), 3.68 (2H, m), 5.00 (1H, q, J=6.3 Hz), 5.40 (1H, m), 6.25 (1H, d, J=16.0 Hz) and 6.60 to 7.10 (4H)

Mass(m/e): 452 (M+)

EXAMPLE 1

11-deoxy-11-acetoxy-16-methyl-18,19-tetradehydro-5,6,7-trinor-4,8-inter-m-phenylene PGI$_2$ To a stirred solution of 122 mg of 11,15-dideoxy-11-acetoxy-16-methyl-15-oxo-18,19-tetradehydro-5,6,7-trinor-4,8-inter-m-phenylene PGI$_2$ in 10 ml of methanol was added 150 mg of cerium chloride heptahydrate, and then the solution was cooled in an ice bath, and 15 mg of sodium borohydride was added to the solution. After 10 min, to the mixture was added 2 ml of aqueous saturated solution of sodium hydrogen carbonate, and the mixture was further stirred for 10 min.

After concentration of the reaction mixture, 5 ml of ethyl acetate was added to the residue, and the precipitate was filtered and washed with ethyl acetate (2×2 ml). The combined organic layers were washed with water and aqueous saturated solution of sodium chloride, dried and concentrated to give 130 mg of an oily material. The oily material was purified by column-chromatography on silicagel using ethyl acetate and cyclohexane (1:2) as eluent to give 54 mg of the captioned compound.

IR(liquid film) $\nu$: 3475, 1740, 1595 and 970 cm$^{-1}$

Mass(m/e): 454 (M+)

EXAMPLE 2

Methyl ester of 16-methyl-18,19-tetradehydro-5,6,7-trinor-4,8-inter-m-phenylene PGI$_2$ To a solution of 54 mg of methyl ester of 11-deoxy-11-acetoxy-16-methyl-18,19-tetradehydro-5,6,7-trinor-4,8-inter-m-phenylene PGI$_2$ in 4.5 ml of anhydrous methanol was added 0.001 ml of 4.8N sodium methoxide under argon, and the reaction mixture was stirred for 1.5 hours at room temperature.

After addition of acetic acid to the reaction mixture and concentration of the mixture, the residue was dissolved in 20 ml of ethyl acetate, and the solution was washed with aqueous saturated solution of sodium hydrogen carbonate, water and aqueous saturated solution of sodium chloride, dried and concentrated to afford 55 mg of an oily material.

This oily material was purified by column chromatography using ethyl acetate and cyclohexane (3:1) as eluent to give 48 mg of the captioned compound.

IR(liquid film) $\nu$: 3370, 1740, 1595, 970 and 745 cm$^{-1}$

NMR(CDCl$_3$) $\delta$: 1.00 (3H, dd, J=6.3 Hz), 1.80 (3H, t, J=3.1 Hz), 1.80 to 2.80 (14H), 3.45 (1H, t, J=7.8 Hz), 3.65 (3H, s), 4.00 (2H, m), 5.10 (1H, m), 5.65 (2H, m) and 6.60 to 7.00 (3H)

Mass(m/e): 412 (M+)

EXAMPLE 3

16-methyl-18,19-tetradehydro-5,6,7-trinor-4,8-inter-m-phenylene PGI$_2$

To a solution of 41 mg of methyl ester of 16-methyl-18,19-tetradehydro-5,6,7-trinor-4,8-inter-m-phenylene PGI$_2$ in 4.3 ml of methanol was added 1 ml of 1N sodium hydroxide, and the mixture was allowed to stand for 17 hours at 30° C. Then the reaction mixture was concentrated, and 1 ml of water was added to the residue. After acidification of the solution to pH 4, the mixture was extracted with three 5 ml portions of ethyl acetate. The extract was washed with 5 ml of water and 5 ml of aqueous saturated solution of sodium chloride, dried and concentrated to give 39 mg of the pure carboxylic acid.

IR(liquid film) $\nu$: 3700 to 2200, 1710, 1595 and 743 cm$^{-1}$

NMR(CDCl$_3$) $\delta$: 1.00 (3H, m), 1.79 (3H, s), 1.50 to 3.00 (12H), 3.35 (1H, t, J=9.1 Hz), 4.00 (2H, m), 5.20 (4H, m), 5.60 (2H, m), 6.80 (1H, m) and 6.90 (2H, m)

Mass(m/e): 398 (M+)

After the oily product had been restored in a refrigerator, it was found that the oily product crystallized extremely slowly. The thus obtained crude crystals were fractionally recrystallized to give 15 mg of 16-β-methyl isomer (m.p.; 123.5° to 124° C.) and 10 mg of 16-α-methyl isomer (m.p.; 92° to 94° C.).

The 16-β-methyl isomer showed the following analytical data.

IR(KBr) $\nu$: 3600 to 2400, 1740, 1680, 1595, 965, 775, 765 and 740 cm$^{-1}$

NMR(CDCl$_3$) δ: 0.97 (3H, d, J=7.2 Hz), 1.80 (3H, t, J=1.5 Hz), 3.40 (3H, t, J=8.3 Hz), 3.95 (2H, m), 4.70 (2H, m), 5.05 (1H, m), 5.60 (2H, m) and 6.83 (3H, m)

Mass(m/e): 398 (M+)

HR Mass(m/e): 398.20850 calcd for C$_{24}$H$_{30}$O$_5$; 398.2093

The 16-α-methyl isomer showed the following analytical data.

IR(KBr) $\nu$: 3600 to 2400, 1710, 1595, 970, 762 and 740 cm$^{-1}$

NMR(CDCl$_3$) δ: 1.05 (3H, d, J=7.2 Hz), 1.80 (3H, t, J=1.5 Hz), 3.40 (1H, t, J=8.3 Hz), 3.85 (1H, m), 4.12 (1H, m), 5.10 (3H, m), 5.65 (2H, m) and 6.85 (3H, m)

Mass(m/e): 398 (M+)

HR Mass(m/e): 398.21347 calcd for C$_{24}$H$_{30}$O$_5$; 398.2093

REFERENCE EXAMPLE 9

Methyl ester of 11,15-dideoxy-11-acetoxy-15-oxo-18,19-tetradehydro-5,6,7-trinor-4,8-inter-m-phenylene PGI$_2$ To a solution of 150 mg of methyl 4-[2-endo-acetoxy-1-exo-hydroxymethyl-3a,8b-cis-2,3,3a,8b-tetrahydro-1H-5-cyclopenta[b]benzofuranyl]butyrate in 122 ml of a solution obtained by dissolving 0.3 ml of anhydrous pyridine in 10 ml of anhydrous benzene were added 0.37 ml of a solution obtained by dissolving 0.14 ml of trifluoroacetic acid in 10 ml of anhydrous dimethylsulfoxide and 340 mg of dicyclohexylcarbodiimide. The resulting mixture was stirred for 14 hours at room temperature, and then the deposited precipitate was removed by filtration and washed well with benzene. The filtrate was washed with three 3 ml portions of water, dried and consentrated to give 260 mg of crude aldehyde.

In the next step, under argon atmosphere to a stirred suspension of 118 mg of sodium hydride (55% dispersion in mineral oil) in 10 ml of dimethoxyethane, was added a solution of 689 mg of dimethyl 2-oxo-hept-5-yne-phosphonate in 10 ml of dimethoxyethane, and the mixture was stirred for 30 mins. To the thus prepared reaction mixture was added a solution of 260 mg of the above-mentioned crude aldehyde in 5 ml of dimethoxyethane, and the mixture was stirred for 30 min at room temperature. After neutralization (pH 7) with acetic acid, the mixture was concentrated.

The residue was dissolved in 10 ml of pentane and ether (1:1), and the precipitate was filtered, and the filtrate was concentrated to give 800 mg of an oily material. The oily material was purified by column chromatography using ethyl acetate and cyclohexane (1:3) as eluent to yield 116 mg of the captioned compound (yield; 62%).

IR(Liquid film) $\nu$: 1740, 1700, 1675, 1630, 1595 and 750 cm$^{-1}$

NMR(CDCl$_3$) δ: 1.69 (3H, t, J=3.1 Hz), 1.71 (3H, s), 1.70 to 3.05 (13H), 3.60 (3H, s), 3.62 (1H, m), 4.90 (1H, q, J=6.2 Hz), 5.15 (1H, m), 6.15 (1H, dd, J=16.0 Hz and 2.0 Hz) and 6.50 to 7.10 (4H, m)

Mass(m/e): 438 (M+)

EXAMPLE 4

Methyl ester of 11-deoxy-11-acetoxy-18,19-tetradehydro-5,6,7-trinor-4,8-inter-m-phenylene PGI$_2$ In a similar manner as in Example 1, from 116 mg of methyl ester of 11,15-dideoxy-11-acetoxy-15-oxo-18,19-tetradehydro-5,6,7-trinor-4,8-inter-m-phenylene PGI$_2$, 56 mg of the captioned compound was obtained with the following analytical data.

IR(Liquid film) $\nu$: 3475, 1740, 1595 and 970 cm$^{-1}$

Mass(m/e): 440 (M+)

EXAMPLE 5

Methyl ester of 18,19-tetradehydro-5,6,7-trinor-4,8-inter-m-phenylene PGI$_2$

In a similar manner as in Example 2, from 56 mg of methyl ester of 11-deoxy-11-acetoxy-18,19-tetradehydro-5,6,7-trinor-4,8-inter-m-phenylene PGI$_2$, 49 mg of the captioned compound was obtained with the following analytical data.

IR(liquid film) $\nu$: 3370, 1740, 1595, 970 and 745 cm$^{-1}$

NMR(CDCl$_3$) δ: 1.70 (3H, t, J=3.0 Hz), 1.20 to 2.80 (15H), 3.40 (1H, t, J=7.8 Hz), 3.59 (3H, s), 3.80 (1H, q, J=6.1 Hz), 4.50 (1H, m), 5.05 (1H, m), 5.60 (2H, m) and 6.60 to 7.00 (3H)

Mass(m/e): 398 (M+)

EXAMPLE 6

18,19-tetradehydro-5,6,7-trinor-4,8-inter-m-phenylene PGI$_2$

In a similar manner as in Example 3, from 43 mg of methyl ester of 18,19-tetradehydro-5,6,7-trinor-4,8-inter-m-phenylene PGI$_2$, 41 mg of the captioned compound was obtained with the following analytical data.

IR(liquid film) $\nu$: 3700 to 2200, 1710, 1595, 975 and 740 cm$^{-1}$

NMR(CDCl$_3$) δ: 1.65 (3H, t, J=3.0 Hz), 1.40 to 2.80 (14H), 3.30 (1H, t, J=8.0 Hz), 3.80 (1H, m), 4.20 (1H, m), 5.00 (1H, m), 5.10 to 5.80 (4H) and 6.5 to 7.00 (3H)

Mass(m/e): 384 (M+)

REFERENCE EXAMPLE 10

Methyl ester of 16-methyl-2-phenylseleno-18,19-tetradehydro-5,6,7-trinor-4,8-inter-m-phenylene PGI$_2$ To a stirred solution of 0.15 ml of diisopropylamine in 10 ml of anhydrous tetrahydrofuran was added at −78° C. 0.7 ml of 1.5N n-butyl lithium, and the mixture was stirred for 15 min. To the thus prepared solution was added at −78° C. a solution of 90 mg of 16-methyl-18,19-tetradehydro-5,6,7-trinor-4,8-inter-m-phenylene PGI$_2$ in 2 ml of anhydrous tetrahydrofuran, and the mixture was stirred at the same temperature for 30 mins. Then, to the mixture was added a solution of 200 mg of diphenyl diselenide in 1 ml of anhydrous HMPA and the whole mixture was stirred for 20 mins at −78° C. Then to the mixture was added solid ammonium chloride and the resulting mixture was stirred for 20 mins at −78° C. and for 10 mins at room temperature. After addition of water, the mixture was extracted three times with ether. The combined organic layers were washed with water and aqueous saturated solution of sodium chloride, dried and concentrated to give 100 mg of an oily material. The oily material was purified by column chromatography on silicagel using ethyl acetate and cyclohexane (3:1) as eluent to afford 87 mg of the captioned compound.

IR(liquid film) ν: 3370, 1735, 1595 and 970 cm$^{-1}$
Mass(m/e): 566 and 568

EXAMPLE 7

Methyl ester of 16-methyl-2,3-didehydro-18,19-tetradehydro-5,6,7-trinor-4,8-inter-m-phenylene PGI$_2$ To a solution of 40 mg of methyl ester of 16-methyl-2-phenylseleno-18,19-tetradehydro-5,6,7-trinor-4,8-inter-m-phenylene PGI$_2$ in 5 ml of ethyl acetate was added 0.16 ml of 35% aqueous hydrogen peroxide solution, and the reaction mixture was stirred for one hour at room temperature. After addition of 1 ml of dimethyl sulfide and 200 mg of potassium acetate to the reaction mixture, the reaction mixture was stirred for 10 min at room temperature, and concentrated under a reduced pressure. After addition of water to the residue, the reaction mixture was extracted three times with ethyl acetate, and the combined extracts were washed with aqueous saturated solution of sodium hydrogen carbonate, water and aqueous saturated solution of sodium chloride, dried and concentrated to give 40 mg of an oily material. The oily material was purified by column chromatography on silicagel using ethyl acetate and cyclohexane (3:1) as eluent to yield 25 mg of the captioned compound (yield; 89%).

IR(liquid film) ν: 3350, 1710, 1650, 1595, 970 and 745 cm$^{-1}$
NMR(CDCl$_3$) δ: 1.00 (3H, dd, J=6.3 Hz), 1.80 (3H, t, J=3.1 Hz), 1.80 to 3.00 (12H), 3.45 (1H, t, J=7.8 Hz), 3.64 (3H, s), 4.00 (2H, m), 5.10 (1H, m), 5.62 (3H, m) and 6.60 to 7.00 (4H)
Mass(m/e): 410 (M$^+$)

REFERENCE EXAMPLE 11

Methyl ester of 2-phenylseleno-18,19-tetradehydro-5,6,7-trinor-4,8-inter-m-phenylene PGI$_2$ In a similar manner as in Reference Example 10, from 80 mg of methyl ester of 18,19-tetradehydro-5,6,7-trinor-4,8-inter-m-phenylene PGI$_2$, 76 mg of the captioned compound was obtained.

IR(liquid film) ν: 3372, 1736, 1594 and 971 cm$^{-1}$
Mass(m/e): 552 and 554

EXAMPLE 8

Methyl ester of 2,3-didehydro-18,19-tetradehydro-5,6,7-trinor-4,8-inter-m-plenylene PGI$_2$ In a similar manner as in Example 7, from 40 mg of methyl ester of 2-phenylseleno-18,19-tetradehydro-5,6,7-trinor-4,8-inter-m-phenylene PGI$_2$, 24 mg of the captioned compound was obtained.

IR(liquid film) ν: 3350, 1710, 1650, 1595, 970 and 745 cm$^{-1}$
NMR(CDCl$_3$) δ: 1.70 (3H, t, J=3.0 Hz), 1.20 to 2.81 (15H), 3.40 (1H, t, J=7.6 Hz), 3.59 (3H, s), 3.80 (1H, q, J=6.0 Hz), 4.52 (1H, m), 5.05 (1H, m), 5.63 (3H, m) and 6.60 to 7.00 (4H)
Mass(m/e): 396 (M$^+$)

REFERENCE EXAMPLE 12

2-phenylseleno-18,19-tetradehydro-5,6,7-trinor-4,8-inter-m-phenylene PGI$_2$

To a solution of 42 mg of methyl ester of 2-phenylseleno-18,19-tetradehydro-5,6,7-trinor-4,8-inter-m-phenylene PGI$_2$ in 4 ml of methanol was added 0.8 ml of 1N sodium hydroxide solution, and the reaction mixture was stirred for 14 hours at room temperature. After concentration of the reaction mixture under a reduced pressure, water was added to the residue. The reaction mixture was cooled in an ice bath, acidified to pH 4 with 1N hydrochloric acid, and extracted three times with ethyl acetate. The combined organic layers were washed with water and aqueous saturated solution of sodium chloride, dried, and concentrated to give 41 mg of the pure captioned compound.

IR(liquid film) ν: 3600 to 2200, 1700, 1595 and 965 cm$^{-1}$
Mass(m/e): 552 and 554

REFERENCE EXAMPLE 13

2-phenylseleno-18,19-tetradehydro-5,6,7-trinor-4,8-inter-m-phenylene PGI$_2$

In a similar manner as in Reference Example 12, from 40 mg of methyl ester of 2-phenylseleno-18,19-tetradehydro-5,6,7-trinor-4,8-inter-m-phenylene PGI$_2$, 38 mg of the captioned compound was obtained.

IR(liquid film) ν: 3600 to 2200, 1700, 1595 and 965 cm$^{-1}$
Mass(m/e): 538 and 540

EXAMPLE 9

16-methyl-2,3-didehydro-18,19-tetradehydro-5,6,7-trinor-4,8-inter-m-phenylene PGI$_2$ To a solution of 41 mg of 16-methyl-2-phenylseleno-18,19-tetradehydro-5,6,7-trinor-4,8-inter-m-phenylene PGI$_2$ in 5 ml of ethyl acetate was added 0.16 ml of aqueous 35% solution of hydrogen peroxide, and the mixture was stirred for 1 hour at room temperature. To the reaction mixture were added 1 ml of dimethyl sulfide and then 100 mg of potassium acetate and the mixture was stirred for 10 min at room temperature. After concentration of the reaction mixture under a reduced pressure, water was added to the residue, and the pH of the mixture was adjusted to 6 with 0.25N hydrochloric acid under ice cooled condition. The mixture was extracted three times with ethyl acetate and the combined organic layers were washed with water and aqueous saturated solution of sodium chloride, dried, and concentrated to give, 34 mg of an oily material. The oily material was purified by column chromatography on acidic silicagel using ethyl acetate and cyclohexane (3:1) as eluent to yield 25 mg of the captioned compound.

IR(liquid film) ν: 3600 to 2200, 1700, 1640, 1600 and 960 cm$^{-1}$
NMR(CDCl$_3$) δ: 1.10 (3H), 1.82 (3H, t, J=3.1 Hz), 1.80 to 3.00 (13H), 3.46 (1H, t, J=7.8 Hz), 4.05 (4H, m), 5.11 (1H, m), 5.66 (3H, m) and 6.60 to 7.00 (4H)
Mass(m/e): 396 (M$^+$)

EXAMPLE 10

2,3-didehydro-18,19-tetradehydro-5,6,7-trinor-4,8-inter-m-phenylene PGI$_2$

In a similar manner as in Example 9, from 38 mg of 2-phenylseleno-18,19-tetradehydro-5,6,7-trinor-4,8-inter-m-phenylene PGI$_2$, 22 mg of the captioned compound was obtained.

IR(liquid film) $\nu$: 3600 to 2200, 1700, 1640, 1600 and 960 cm$^{-1}$

NMR(CDCl$_3$) δ: 1.80 (3H, t, J=3.1 Hz), 1.80 to 3.00 (13H), 3.45 (1H, t, J=7.8 Hz), 4.00 (4H, m), 5.11 (1H, m), 5.65 (3H, m) and 6.60 to 7.00 (4H)

Mass(m/e): 382 (M+)

REFERENCE EXAMPLE 14

Methyl ester of 11,15-dideoxy-11-acetoxy-16,20-dimethyl-18,19-tetradehydro-5,6,7-trinor-4,8-inter-m-phenylene PGI$_2$ In a similar manner as in Reference Example 8 except for using dimethyl 3-methyl-2-oxo-oct-5-yne-phosphonate instead of dimethyl 3-methyl-2-oxo-hept-5-yne-phosphonate, from 150 mg of methyl 4-[2-endo-acetoxy-1-exo-hydroxymethyl-3a,8b-cis-2,3,3a,8b-tetrahydro-1H-5-cyclopenta[b]benzofuranyl]butyrate, 120 mg of the captioned compound was obtained.

IR(liquid film) $\nu$: 1740, 1700, 1670, 1630, 1595 and 970 cm$^{-1}$

Mass(m/e): 466 (M+)

REFERENCE EXAMPLE 15

Methyl ester of 11,15-dideoxy-11-acetoxy-20-butyl-16-methyl-15-oxo-18,19-tetradehydro-5,6,7-trinor-4,8-inter-m-phenylene PGI$_2$ In a similar manner as in Reference Example 8 except for using dimethyl 3-methyl-2-oxo-undec-5-yne-phosphonate instead of dimethyl 3-methyl-2-oxo-hept-5-yne-phosphonate, from 150 mg of methyl 4-[2-endo-acetoxy-1-exo-hydroxymethyl-3a,8b-cis-2,3,3a,8b-tetrahydro-1H-5-cyclopenta[b]benzofuranyl]butyrate, 100 mg of the captioned compound was obtained.

IR(liquid film) $\nu$: 1740, 1700, 1670, 1630, 1595 and 975 cm$^{-1}$

Mass(m/e): 508

EXAMPLE 11

Methyl ester of 11-deoxy-11-acetoxy-16,20-dimethyl-18,19-tetradehydro-5,6,7-trinor-4,8-inter-m-phenylene PGI$_2$ In a similar manner as in Example 1, from 130 mg of methyl ester of 11,15-dideoxy-11-acetoxy-1,20-dimethyl-15-oxo-18,19-tetradehydro-5,6,7-trinor-4,8-inter-m-phenylene PGI$_2$, 58 mg of the captioned compound was obtained.

IR(liquid film) $\nu$: 3475, 1740, 1595 and 970 cm$^{-1}$

Mass(m/e): 468 (M+)

EXAMPLE 12

Methyl ester of 16,20-dimethyl-18,19-tetradehydro-5,6,7-trinor-4,8-inter-m-PGI$_2$ In a similar manner as in Example 2, from 58 mg of methyl ester of 11-deoxy-11-acetoxy-16-methyl-18,19-tetradehydro-5,6,7-trinor-4,8-inter-m-phenylene PGI$_2$, 50 mg of the captioned compound was obtained.

IR(liquid film) $\nu$: 3370, 1740, 1595 and 970 cm$^{-1}$

Mass(m/e): 426 (M+)

EXAMPLE 13

16,20-dimethyl-18,19-tetradehydro-5,6,7-trinor-4,8-inter-m-phenylene PGI$_2$

In a similar manner as in Example 3, from 50 mg of methyl ester of 16,20-dimethyl-18,19-tetradehydro-5,6,7-trinor-4,8-inter-m-phenylene PGI$_2$, 48 mg of the captioned compound was obtained.

IR(liquid film) $\nu$: 3700 to 2200, 1710, 1595 and 975 cm$^{-1}$

Mass(m/e): 412 (M+)

EXAMPLE 14

Methyl ester of 11-deoxy-11-acetoxy-20-butyl-16-methyl-18,19-tetradehydro-5,6,7-trinor-4,8-inter-m-phenylene PGI$_2$ In a similar manner as in Example 1, from 120 mg of methyl ester of 11,15-dideoxy-11-acetoxy-20-butyl-16-methyl-15-oxo-18,19-tetradehydro-5,6,7-trinor-4,8-inter-m-phenylene PGI$_2$, 50 mg of the captioned compound was obtained.

IR(liquid film) $\nu$: 3473, 1740, 1595 and 970 cm$^{-1}$

Mass(m/e): 510 (M+)

EXAMPLE 15

Methyl ester of 20-butyl-16-methyl-18,19-tetradehydro-5,6,7-trinor-4,8-inter-m-phenylene PGI$_2$ In a similar manner as in Example 2, from 50 mg of methyl ester of 11-deoxy-11-acetoxy-20-butyl-16-methyl-18,19-tetradehydro-5,6,7-trinor-4,8-inter-m-phenylene PGI$_2$, 44 mg of the captioned compound was obtained.

IR(liquid film) $\nu$: 3372, 1740, 1595, 970 and 745 cm$^{-1}$

Mass(m/e): 468 (M+)

EXAMPLE 16

20-butyl-16-methyl-18,19-tetradehydro-5,6,7-trinor-4,8-inter-m-phenylene PGI$_2$ In a similar manner as in Example 3, from 44 mg of methyl ester of 20-butyl-16-methyl-18,19-tetradehydro-5,6,7-trinor-4,8-inter-m-phenylene PGI$_2$, 42 mg of the captioned compound was obtained.

EXAMPLE 17

Sodium salt of 16-methyl-18,19-tetradehydro-5,6,7-trinor-4,8-inter-m-phenylene PGI$_2$ To a solution of 100 mg of 16-methyl-18,19-tetradehydro-5,6,7-trinor-4,8-inter-m-phenylene PGI$_2$ in methanol was added 0.25 ml of an aqueous 1N solution of sodium hydroxide, and the reaction mixture was stirred for 10 min under ice cooled condition, and concentrated to give 105 mg of the captioned compound.

IR(KBr) $\nu$: 3400, 1605 and 1595 cm$^{-1}$

In a similar manner as above, from 16,20-dimethyl-18,19-tetradehydro-5,6,7-trinor-4,8-inter-m-phenylene PGI$_2$ instead of 16-methyl-18,19-tetradehydro-5,6,7-trinor-4,8-inter-m-phenylene PGI$_2$, sodium salt of 16,20-dimethyl-18,19-tetradehydro-5,6,7-trinor-4,8-inter-m-phenylene PGI$_2$ is obtained, and from 20-butyl-16-methyl-18,19-tetradehydro-5,6,7-trinor-4,8-inter-m-phenylene PGI$_2$ instead of 16-methyl-18,19-tetradehydro-5,6,7-trinor-4,8-inter-m-phenylene PGI$_2$, sodium salt of 20-butyl-16-methyl-18,19-tetradehydro-5,6,7-trinor-4,8-inter-m-phenylene PGI$_2$ is obtained.

EXAMPLE 18

Triethanolamine salt of 16-methyl-18,19-tetradehydro-5,6,7-trinor-4,8-inter-m-phenylene PGI$_2$ To a solution of 100 mg of 16-methyl-18,19-tetradehydro-5,6,7-trinor-4,8-inter-m-phenylene PGI$_2$ in 5 ml of methanol was added 38 mg of triethanolamine. The reaction mixture was stirred for 10 mins at room temperature and concentrated to give 137 mg of the captioned compound.

IR(liquid film) $v$: 3400, 1604 and 1595 cm$^{-1}$

In a similar manner as above, from 16,20-dimethyl-18,19-tetradehydro-5,6,7-trinor-4,8-inter-m-phenylene PGI$_2$ instead of 16-methyl-18,19-tetradehydro-5,6,7-trinor-4,8-inter-m-phenylene PGI$_2$, the triethanolamine salt of 16,20-dimethyl-18,19-tetradehydro-5,6,7-trinor-4,8-inter-m-phenylene PGI$_2$ is obtained and from 20-butyl-16-methyl-18,19-tetradehydro-5,6,7-trinor-4,8-inter-m-phenylene PGI$_2$ instead of 16-methyl-18,19-tetradehydro-5,6,7-trinor-4,8-inter-m-phenylene PGI$_2$, the triethanolamine salt of 20-butyl-16-methyl-18,19-tetradehydro-5,6,7-trinor-4,8-inter-m-phenylene PGI$_2$ is obtained.

REFERENCE EXAMPLE 16

2-butyn-1-ol

A mixture of 250 g of 1,3-dichloro-2-butene and 1.25 liters of aqueous 10% by weight solution of sodium carbonate was refluxed for 3 hours and then cooled. The reaction mixture was extracted three times with ether, and the extract was dried. The ether was distilled off at atmospheric pressure using Widmer column, and then the residue was distilled under reduced pressure to give 134 g of 3-chloro-2-buten-1-ol (b.p. 58°-60° C./8 mmHg).

In the next step, into a flask provided with a Duwar-condenser was introduced 3 liters of liquid ammonia, and 1.5 g of ferric nitrate was added to the liquid ammonia with stirring and then 65 g of metallic sodium was added in several points. To the mixture was added over 30 mins 134 g of the above-mentioned 3-chloro-2-buten-1-ol, and the mixture was stirred for 14 hours. After addition of 148 g of ammonium chloride, the mixture was stirred for 30 mins, and the ammonia was removed from the reaction mixture.

Then, the residue was extracted five times with ether, and the ether was distilled off using Vigreaux column, and the residue was distilled under reduced pressure to give 66 g of 2-butyn-1-ol (b.p. 55° C./8 mmHg).

IR(liquid film) $v$: 3350, 2230, 1145 and 1050 cm$^{-1}$

NMR(CDCl$_3$) δ: 1.84 (3H, t, J=3.0 Hz), 2.60 (1H, s) and 4.24 (2H)

REFERENCE EXAMPLE 17

1-bromo-2-butyne

To a solution of 63 g of 2-butyn-1-ol in 250 ml of anhydrous ether was added 5 ml of pyridine, and the solution was stirred at −30° C. To the thus cooled solution was added dropwise 86 g of phosphorus tribromide, and the mixture was stirred for 2 hours at −30° C. Then, the temperature of the reaction mixture was raised to 20° C. over 3 hours and stirred for 30 mins at 40° C. The mixture was poured into 500 ml of an aqueous saturated solution of sodium chloride, and upper layer was separated from aqueous layer. The aqueous layer was extracted with a small amount of ether and the combined ethereal solution was dried. The ether was disilled off through a 40 cm-Widmer column under atmospheric pressure, and then the residue was distilled under reduced pressure to yield 95 g of 1-bromo-2-butyne (60° C./80 mmHg).

IR(liquid film) $v$: 2240, 1220 and 1210 cm$^{-1}$

NMR(CDCl$_3$) δ: 1.85 (3H, t, J=3.0 Hz) and 3.90 (2H, m)

REFERENCE EXAMPLE 18

Dimethyl 3-methyl-2-oxo-hept-5-yne-phosphonate

To a solution of 30 g of diisopropylamine in 186 ml of anhydrous tetrahydrofuran was slowly added at −20° C. 182.3 ml of 1.51N n-butyl lithium, and the mixture was stirred at the same temperature for 20 mins. Then, to the mixture were slowly added dropwise in the range from −20° to −10° C. 12 g of propionic acid and 25 ml of HMPA. The temperature of the reaction mixture was raised to room temperature and the mixture was stirred for 40 mins, and then 16.7 g of 1-bromo-2-butene was added dropwise at 0° C. to the mixture. After being stirred for 2 hours, the mixture was poured into 130 ml of aqueous 10% solution of hydrochloric acid, and the mixture was extracted three times with mixture of ether and pentane (1:1). The combined organic layers were washed with water, dried and concentrated to give an oily material. The thus obtained oily material was esterified by the addition of an excess of ethereal solution of diazomethane. After concentration of the mixture, the residue was distilled under reduced pressure to yield 10.4 g of the ester (60° to 70° C./11 mmHg).

Next, to a solution of 18 g of dimethyl methanephosphonate in 294 ml of anhydrous tetrahydrofuran was added at −78° C. 86 ml of n-butyl lithium (1.5N), and the mixture was stirred for 20 mins. To the thus prepared reaction mixture was added a solution of 10.4 g of the above-mentioned ester in 20 ml of anhydrous tetrahydrofuran. Then, the mixture was stirred for 15 mins at −78° C. and for 1 hour at room temperature, and 300 ml of ether was added. The solution was washed with 150 ml of aqueous saturated solution of oxalic acid, 150 ml of water and 50 ml of aqueous saturated solution of sodium chloride and condensed. The residue was distilled under a reduced pressure to give 14.7 g of dimethyl 3-methyl-2-oxo-hept-5-yne-phosphonate (138° to 142° C./0.62 mmHg).

IR(liquid film) $v$: 3450, 1715, 1255 and 1030 cm$^{-1}$

NMR(CDCl$_3$) δ: 1.15 (3H, d, J=6.0 Hz), 1.75 (3H, t, J=3.0 Hz), 2.35 (2H, m), 2.90 (1H, m), 3.20 (2H, d, J=18.8 Hz), 3.75 (3H, s) and 3.80 (3H, s)

REFERENCE EXAMPLE 19

Dimethyl 2-oxo-hept-5-yne-phosphonate

To a stirred solution of 7.78 g of diisopropylamine in 115 ml of anhydrous tetrahydrofuran was added at −10° C. 49 ml of n-butyl lithium (1.59N). The mixture was stirred for 20 mins at 0° C. To the thus prepared reaction mixture was added dropwise at 0° C. 2.34 g of acetic acid, and the mixture was stirred for 40 mins in the range from 30° to 35° C. To the mixture were added dropwise at 0° C. 6.1 ml of HMPA and further 4 g of 1-bromo-2-butene. After stirring for 14 hours at room temperature, the mixture was poured into 25 ml of aqueous 10% hydrochloric acid solution, and the mixture was extracted three times wih mixture of pentane and ether (1:1). The organic layer was washed with water, dried and concentrated to give an oily material. The oily material was methylated by addition of an excess of a solution of diazomethane in ether. The reaction mixture was concentrated and distilled under reduced pressure to yield 1.6 g of an ester (boiling at 66° to 70° C./11 mmHg).

To a solution of 3.2 g of dimethyl methanephosphonate in 52 ml of tetrahydrofuran was added at −78° C. 155 ml of n-butyl lithium (1.59N) and the mixture was stirred for 25 mins at −78° C. To the mixture was added at −78° C. a solution of 1.6 g of the above-mentioned ester in 3.2 ml of tetrahydrofuran. The mixture was stirred for 15 mins and for one hour at room temperature. After addition of 100 ml of ether to the reaction mixture, the mixture was washed with 30 ml of aqueous saturated solution of oxalic acid, 50 ml of water and 40 ml of aqueous saturated solution of sodium chloride. The washed mixture was dried and concentrated to give an oily material. The oily material was distilled under reduced pressure to yield 2.2 g of dimethyl 2-oxo-hept-5-yne-phosphonate (143° to 146° C./0.7 mmHg).

IR(liquid film) $\nu$: 3450, 1720, 1250 and 1040 cm$^{-1}$

NMR(CDCl$_3$) $\delta$: 1.75 (3H, t, J=3.0 Hz), 2.45 (2H, m), 2.80 (2H, m), 3.15 (2H, d, J=18.8 Hz), 3.72 (3H, s) and 3.85 (3H, s)

REFERENCE EXAMPLE 20

(+)-7-bromo-3a,8b-cis-3a,8b-dihydro-3H-5-cyclopenta[b]benzofurancarboxylic acid

In 30 ml of a mixture of methanol and water (1:1) were dissolved by heating 1.00 g (3.56 mmol) of (±)-7-bromo-3a,8b-cis-3a,8b-dihydro-3H-5-cyclopenta[b]benzofurancarboxylic acid and 0.78 g (3.56 mmol) of (−)-(cis-2-benzylaminocyclohexyl)methanol. The solution was cooled to room temperature, seeded with the salt of the captioned compound with (−)-(cis-2-benzylaminocyclohexyl)methanol, and allowed to stand for 24 hours. The thus obtained crystals were filtered and recrystallized from 30 ml of a mixture of methanol and water to give 0.68 g of the salt of the captioned compound with (−)-(cis-benzylaminocyclohexyl)methanol (m.p.; 184° to 185° C., yield; 76%, $[\alpha]_D^{22}$=+93° (C=1.5, in methanol)).

After addition of 50 ml of ethyl acetate and 150 ml of 1N aqueous hydrochloric acid solution to the crystals, the layer of ethyl acetate was washed with water and concentrated to yield 0.37 g of the captioned compound (m.p.; 207° to 209° (sublimation), $[\alpha]_D^{22}$=+174° (C=0.4, in methanol), yield; 74%).

REFERENCE EXAMPLE 21

(−)-7-bromo-3a,8b-cis-3a,8b-dihydro-3H-5-cyclopenta[b]benzofurancarboxylic acid

In 100 ml of a 2:1 by volume mixture of methanol and water were dissolved by heating 2.00 g (7.1 mmol) of (±)-7-bromo-3a,8b-cis-3a,8b-dihydro-3H-5-cyclopenta[b]benzofurancarboxylic acid and 2.09 g (7.1 mmol) of cinchonidine. The solution was cooled to a room temperature, seeded with cinchonidine salt of the captioned compound, and allowed to stand for 24 hours. The thus precipitated crystals was collected by filtration and recrystallized from 30 ml of the mixed solvent of methanol and water to give 1.01 g of the cinchonidine salt of the captioned compound (yield; 49%, m.p.; 194° to 195° C., $[\alpha]_D^{22}$=−118° (C=1.0, in methanol).

The thus obtained crystalline salt was dissolved in 20 ml of ethanol, and after addition of 3.5 ml of aqueous 1N hydrochloric acid solution to the solution, the ethanol was distilled off. To the thus obtained residue were added 20 ml of ethyl acetate and 20 ml of 1/10N hydrochloric acid. The organic layer was collected, washed with water and concentrated to yield 0.48 g of the captioned compound (yield; 48%, m.p.; 207° to 209° C. (sublimation); $[\alpha]_D^{22}$=−174° (C=0.4, in methanol)).

EXAMPLE 19

(+)-16-methyl-18,19-tetradehydro-5,6,7-trinor-4,8-inter-m-phenylene PGI$_2$

By following Reference Examples 1 to 8 and Examples 1 to 3, from 5 g of (−)-7-bromo-3a,8b-cis-3a,8b-dihydro-3H-5-cyclopenta[b]benzofurancarboxylic acid as the starting material, 3 mg of the captioned compound is obtained.

IR(liquid film) $\nu$: 3700 to 2200, 1710, 1595 and 743 cm$^{-1}$

NMR(CDCl$_3$) $\delta$: 1.00 (3H, m), 1.79 (3H, s), 1.50 to 3.00 (12H), 3.35 (1H, t, J=9.1 Hz), 4.00 (2H, m), 6.80 (1H, m) and 6.90 (2H, m)

(Mass(m/e): 398 (M+)

EXAMPLE 20

(−)-16-methyl-18,19-tetradehydro-5,6,7-trinor-4,8-inter-m-phenylene PGI$_2$

By following Reference Examples 1 to 8 and Examples 1 to 3, from 5 g of (+)-7-bromo-3a,8b-cis-dihydro-3H-5-cyclopenta[b]benzofurancarboxylic acid, 3.4 mg of the captioned compound is obtained.

IR(liquid film) $\nu$: 3700 to 2200, 1710, 1595 and 743 cm$^{-1}$

NMR(CDCl$_3$) $\delta$: 1.00 (3H, m), 1.79 (3H, s), 1.50 to 3.00 (12H), 3.35 (1H, t, J=9.1 Hz), 4.00 (2H, m), 6.80 (1H, m) and 6.90 (2H, m)

Mass(m/e): 398 (M+)

EXAMPLE 21

(+)-18,19-tetradehydro-5,6,7-trinor-4,8-inter-m-phenylene PGI$_2$

By following Reference Examples 1 to 7 and 9 and Examples 4 to 6, from 5 g of (−)-7-bromo-3a,8b-dihydro-3H-5-cyclopenta[b]benzofurancarboxylic acid, 3.2 mg of the captioned compound is obtained.

IR(liquid film) $\nu$: 3700 to 2200, 1710, 1595, 975 and 740 cm$^{-1}$

NMR(CDCl$_3$) $\delta$: 1.65 (3H, t, J=3.0 Hz), 1.40 to 2.80 (14H), 3.30 (1 H, t, J=8.0 Hz), 3.80 (1H, m), 4.20 (1H, m), 5.00 (1H, m), 5.10 to 5.80 (4H) and 6.50 to 7.00 (3H)

Mass(m/e): 384 (M+)

EXAMPLE 22

(−)-18,19-tetradehydro-5,6,7-trinor-4,8-inter-m-phenylene PGI$_2$

By following Reference Examples 1 to 7 and 9 and Examples 4 to 6, from 5 g of (+)-7-bromo-3a,8b-cis-3a,8b-dihydro-3H-5-cyclopenta[b]benzofurancarboxylic acid, 3.1 mg of the captioned compound is obtained.

IR(liquid film) $\nu$: 3700 to 2200, 1710, 975 and 740 cm$^{-1}$

NMR(CDCl$_3$) $\delta$: 1.65 (3H, t, J=3.0 Hz), 1.40 to 2.80 (14H), 3.30 (1H, t, J=8.0 Hz), 3.80 (1H, m), 4.20 (1H, m), 5.00 (1H, m), 5.10 to 5.80 (4H) and 6.50 to 7.00 (3H)

Mass(m/e): 384 (M+)

EXAMPLE 23

(+)-16(S)-methyl-18,19-tetradehydro-5,6,7-trinor-4,8-inter-m-phenylene PGI₂

By following Reference Example 8 and Examples 1 to 3, from 2.2 g of methyl ester of (+)-4-[2-endo-acetoxy-1-exohydroxymethyl-3a,8b-cis-2,3,3a,8b-tetrahydro-1H-5-cyclopenta[b]benzofuranyl]butyrate and 2.2 g of dimethyl 3(S)-3-methyl-2-oxo-hept-5-yne-phosphonate having a specific rotation of +29.8° $[\alpha]_D^{22}$ (C=4.5, in ethanol)), 450 mg of the captioned compound was obtained in a crude state. The crude product was recrystallized from ethyl acetate and hexane to yield 112 mg of the pure compound (m.p.; 64° to 66° C.).

IR(Kbr) ν: 3700 to 2200, 1712, 1595, 1255, 1235, 1195 1155, 1105, 1095, 1075, 1035, 1015, 1000, 962, 865, 835, 765 and 745 cm⁻¹

NMR(CDCl₃) δ: 0.97 (3H, d, J=7.2 Hz), 1.08 (3H, t, J=1.5 Hz), 3.40 (3H, t, J=8.3 Hz), 3.95 (2H, m), 5.00 (4H, m), 5.60 (2H, m), 6.75 (1H, m) and 6.70 (2H, m)

¹³C NMR(CDCl₃) δ: 3.521 15.737 22.401 24.622 29.118 38.193 41.119 50.246 58.806 75.627 77.036 77.198 78.471 84.214 120.565 121.865 123.274 128.962 129.666 133.350 134.054 and 157.268

Mass(m/e): 398 (M⁺)

$[\alpha]_D^{22}$ (C=0.7, methanol): +120.6°.

EXAMPLE 24

(+)-16(R)-methyl-18,19-tetradehydro-5,6,7-trinor-4,8-inter-m-phenylene PGI₂

By following Reference Example 8 and Examples 1 to 3, from 200 mg of methyl (+)-4-[2-endo-acetoxy-1-exo-hydroxymethyl-3a,8b-cis-2,3,3a,8b-tetrahydro-1H-5-cyclopenta[b]benzofuranyl]butyrate and 230 mg of dimethyl 3(R)-3-methyl-2-oxo-hept-5-yne-phosphonate having a specific rotation of −28.6° ($[\alpha]_D^{22}$ (C=4.8, in ethanol)), 47 mg of the captioned compound was obtained.

IR(liquid film) ν: 3600 to 2400, 1710, 1595, 970, 762 and 740 cm⁻¹

¹H NMR(CDCl₃) δ: 1.05 (3H, d, J=7.2 Hz), 1.80 (3H, t, J=1.5 Hz), 3.40 (1H, t, J=8.3 Hz), 3.85 (1H, m), 4.12 (1H, m), 5.10 (3H, m), 5.65 (2H, m) and 6.85 (3H, m)

Mass(m/e): 398 (M⁺)

$[\alpha]_D^{22}$ (C=0.47, methanol): +110.3°

What is claimed is:

1. A compound of the formula

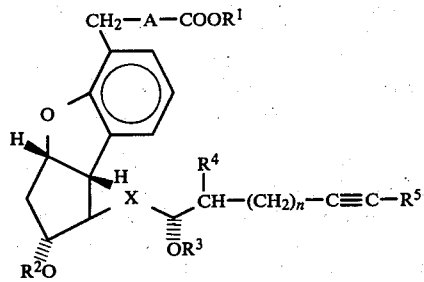

wherein $R^1$ is a pharmaceutically acceptable cation, a hydrogen atom or a n-alkyl group of 1 to 12 carbon atoms; $R^2$ is a hydrogen atom, an acyl group of 2 to 10 carbon atoms or an aroyl group of 7 to 13 carbon atoms; $R^3$ is a hydrogen atom, an acyl group of 2 to 10 carbon atoms or an aroyl group of 7 to 13 carbon atoms; $R^4$ is a hydrogen atom, a methyl group or an ethyl group; $R^5$ is a n-alkyl group of 1 to 5 carbon atoms; n is an integer of 0 to 4; A is —CH₂—CH₂— or trans —CH=CH—; and X is —CH₂—CH₂— or trans —CH=CH—.

2. The compound as defined in claim 1 which is 16-methyl-18,19-tetradehydro-5,6,7-trinor-4,8-inter-m-phenylene prostaglandin I₂ or methyl ester thereof.

3. The compound as defined in claim 1 which is 18,19-tetradehydro-5,6,7-trinor-4,8-inter-m-phenylene prostaglandin I₂ or methyl ester thereof.

4. The compound as defined in claim 1 which is 20-methyl-18,19-tetradehydro-5,6,7-trinor-4,8-inter-m-phenylene prostaglandin I₂ or methyl ester thereof.

5. The compound as defined in claim 1 which is 16,20-dimethyl-18,19-tetradehydro-5,6,7-trinor-4,8-inter-m-phenylene prostaglandin I₂ or methyl ester thereof.

6. The compound as defined in claim 1 which is 20-ethyl-16-methyl-18,19-tetradehydro-5,6,7-trinor-4,8-inter-m-phenylene prostaglandin I₂ or methyl ester thereof.

7. The compound as defined in claim 1 which is 16-methyl-2,3-didehydro-18,19-tetradehydro-5,6,7-trinor-4,8-inter-m-phenylene prostaglandin I₂ or methyl ester thereof.

8. The compound as defined in claim 1 which is 2,3-didehydro-18,19-tetradehydro-5,6,7-trinor-4,8-inter-m-phenylene prostaglandin I₂.

9. The compound as defined in claim 1 which is 16-methyl-13,14-dihydro-18,19-tetradehydro-5,6,7-trinor-4,8-inter-m-phenylene prostaglandin I₂ or methyl ester thereof.

10. The compound as defined in claim 1 which is 20-methyl-19,20-tetradehydro-5,6,7-trinor-4,8-inter-m-phenylene prostaglandin I₂.

11. The compound as defined in claim 1 which is 17,18-tetradehydro-5,6,7-trinor-4,8-inter-m-phenylene prostaglandin I₂.

12. A pharmaceutical composition for use as an antiulceric drug comprising a compound of claim 1 in association with a pharmaceutically acceptable carrier in sufficient amount to provide from 0.01 to about 50 mg of said compound per dose.

13. A pharmaceutical composition for use as a hypotensive agent comprising a compound of claim 1 in association with a pharmaceutically acceptable carrier in sufficient amount to provide from 0.01 to 50 mg per dose.

14. A pharmaceutical composition for use as an antithrombotic agent comprising a compound of claim 1 in association with a pharmaceutically acceptable carrier in sufficient amount to provide from 0.001 to about 50 mg per dose.

* * * * *